United States Patent [19]

Cohen

[11] Patent Number: 4,986,270

[45] Date of Patent: * Jan. 22, 1991

[54] HEMODYNAMICALLY RESPONSIVE SYSTEM FOR AND METHOD OF TREATING A MALFUNCTIONING HEART

[75] Inventor: Todd J. Cohen, Mountain View, Calif.

[73] Assignee: Leonard Bloom, Towson, Md. ; a part interest

[ * ] Notice: The portion of the term of this patent subsequent to Oct. 4, 2005 has been disclaimed.

[21] Appl. No.: 347,450

[22] Filed: May 4, 1989

Related U.S. Application Data

[63] Continuation-in-part of Ser. No. 233,367, Aug. 18, 1988, which is a continuation-in-part of Ser. No. 105,030, Oct. 6, 1987, Pat. No. 4,774,950.

[51] Int. Cl.$^5$ .............................................. A61N 1/00
[52] U.S. Cl. ......................... 128/419 D; 128/419 PG
[58] Field of Search ......... 128/419 D, 419 P, 419 PG

[56] References Cited

U.S. PATENT DOCUMENTS

| | | | |
|---|---|---|---|
| 4,770,177 | 9/1988 | Schroeppel | 128/419 PG |
| 4,774,950 | 10/1988 | Cohen | 128/419 D |
| 4,802,481 | 2/1989 | Schroeppel | 128/419 PG |

*Primary Examiner*—Francis Jaworski
*Assistant Examiner*—George Manuel
*Attorney, Agent, or Firm*—Leonard Bloom

[57] ABSTRACT

A system for and method of treating a malfunctioning heart is based on hemodynamics, the pressure at a site in a patient's circulatory system being sensed. A signal is developed representative of short term mean arterial pressure (MAP), mean right atrial pressure (MRAP), mean right ventrical pressure (MRVP), mean left atrial pressure (MLAP), mean left ventricle pressure (MLVP), mean central venous pressure (MCVP), mean pulmonary artery pressure (MPAP), mean pulmonary vein pressure (MPVP) or mean pulmonary capillary wedge pressure (MPCWP). A signal representative of fixed baseline pressure is provided and if the short term current mean pressure differs therefrom by a predetermined value, an indication of hemodynamic compromise, cardioversion/defibrillation is effected. In a second embodiment, the determination of whether the difference between fixed or varying the baseline pressure and mean current pressure is undertaken after a rate criteria (for example a heart rate above 155 b.p.m.) has been met. In a third embodient, the rate and pressure criteria both must exist at the same time, before cardioverting/-defibrillation is initiated. In a fourth embodiment, a microprocessor is used. The system may be integrated with antitachycardia and/or antibradycardia pacemakers.

37 Claims, 28 Drawing Sheets

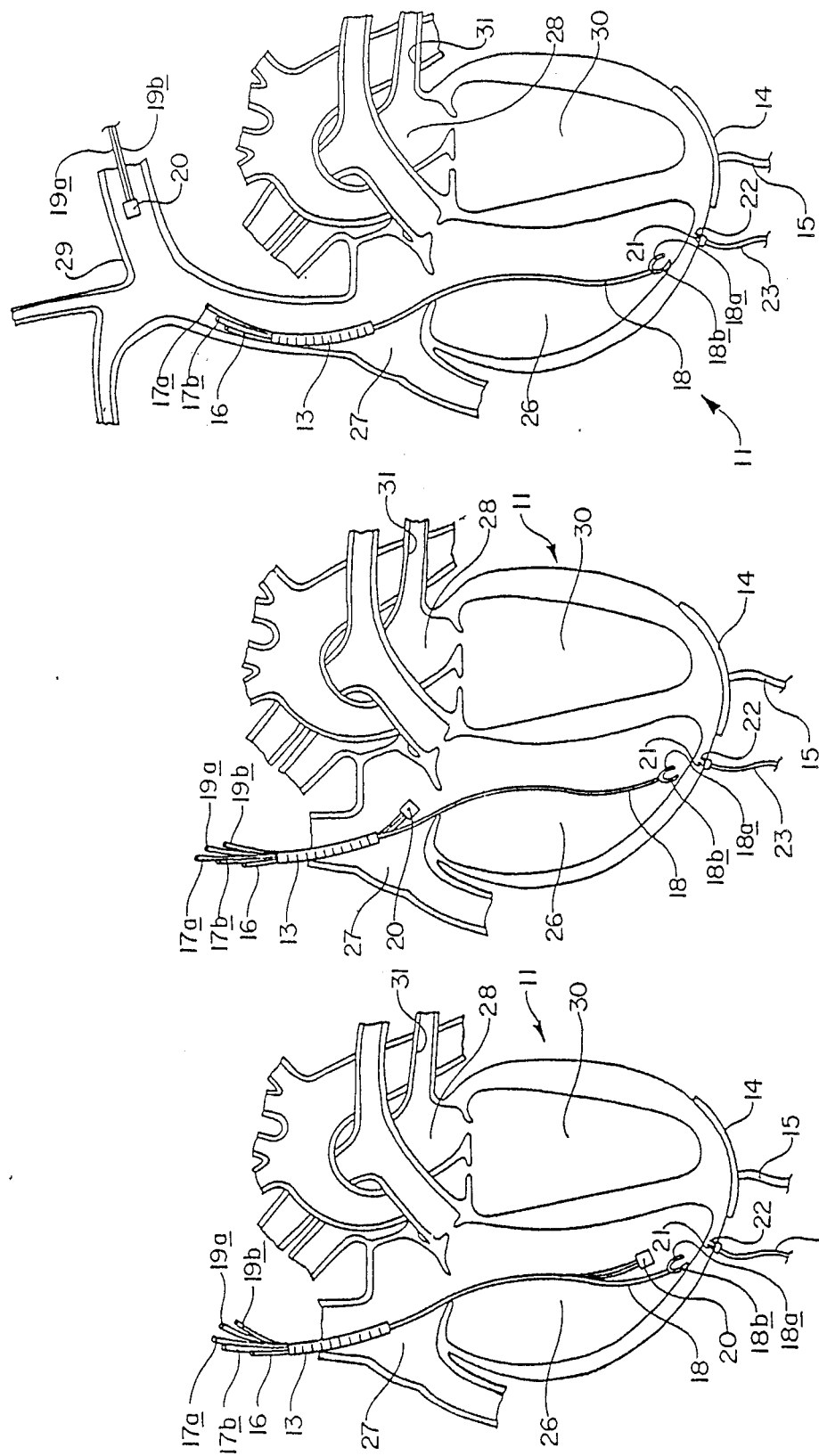

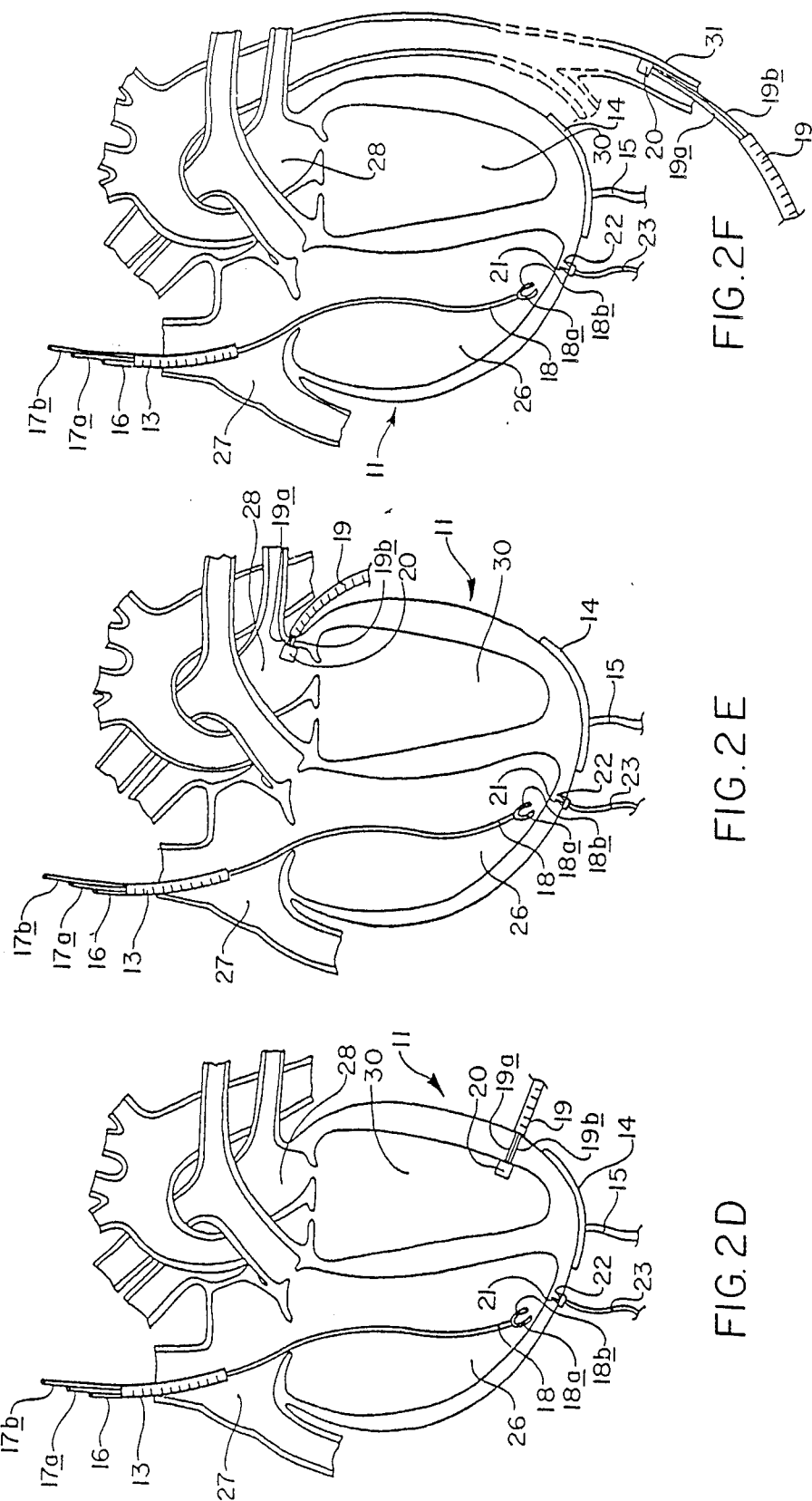

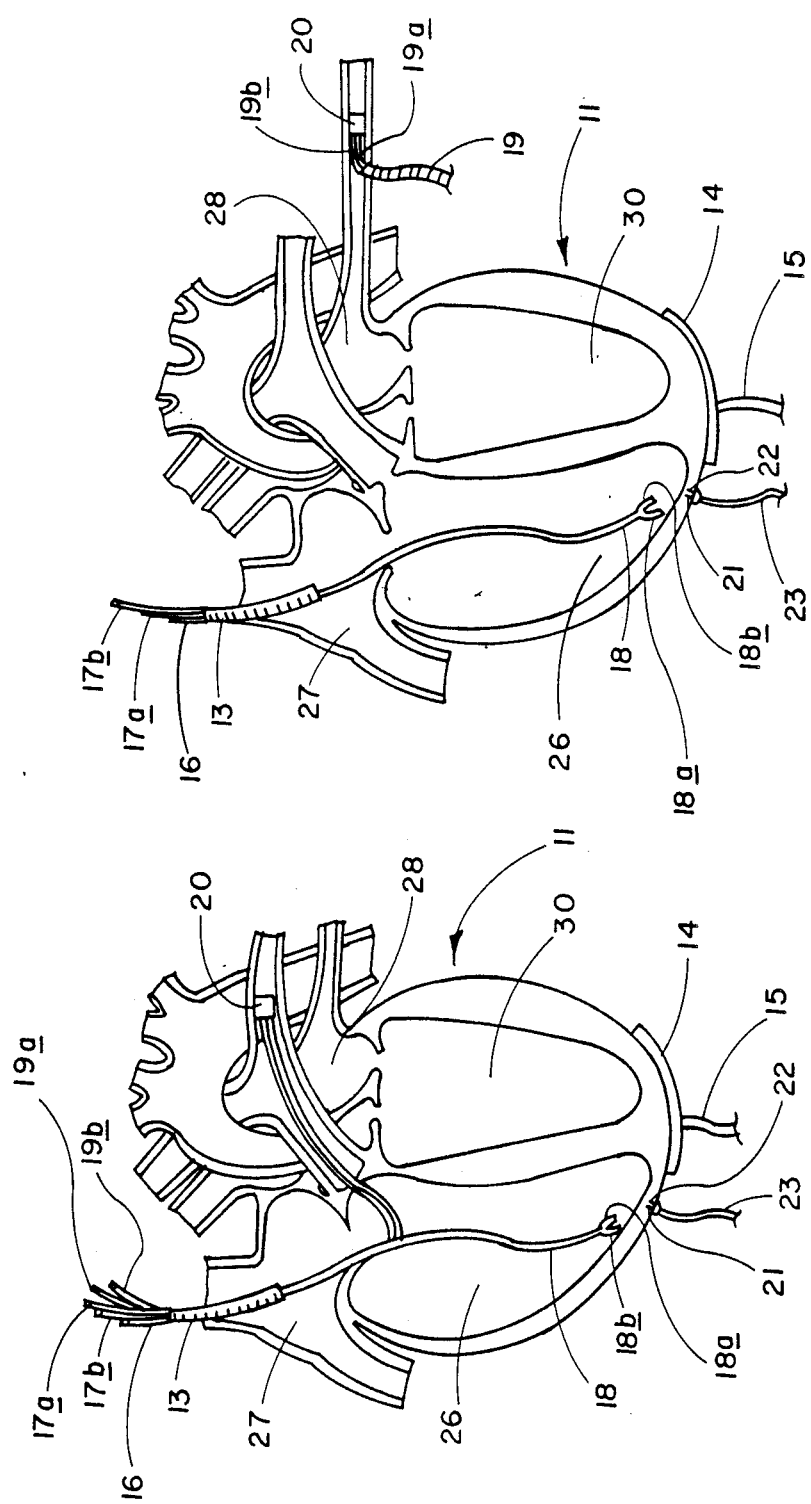

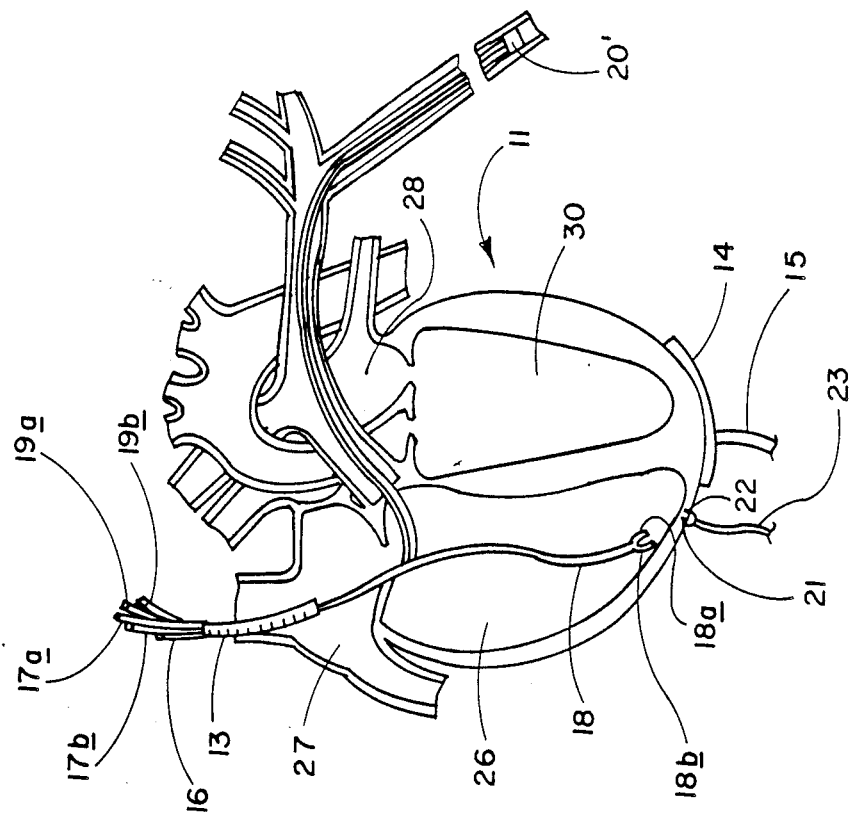

CONFER FIG. 7B

CONFER FIG. 16 B

HEMODYNAMICALLY RESPONSIVE SYSTEM FOR AND METHOD OF TREATING A MALFUNCTIONING HEART

CROSS REFERENCE TO RELATED APPLICATION

This application is a continuation-in-part of copending application Ser. No. 233,367 of Todd J. Cohen filed Aug. 18, 1988 and entitled "Hemodynamically Responsive System for and Method of Treating a Malfunctioning Heart" which is a continuation-in-part of Ser. No. 105,030 of Todd J. Cohen filed on Oct. 6, 1987 and entitled "Hemodynamically Response System for and Method of Treating a Malfunctioning Heart", which has matured as U.S. Pat. No. 4,774,950 granted Oct. 4, 1988. The disclosures of the two prior applications are incorporated herein in their entirety respectively by reference.

BACKGROUND OF THE INVENTION

1. Field of the Invention

This invention relates to a system for and method of treating a malfunctioning heart and, more particularly, to such a system and method which effects cardioversion/defibrillation in response to sensing a heart malfunction. The invention provides for the cardioverting/defibrillation of a malfunctioning heart as well as the possibility of overcoming a tachycardia manifestation without resorting to either cardioverting or defibrillating the heart.

2. Description of the Prior Art

In recent years, substantial progress has been made in pacemakers and in the development of cardioverting/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U.S. Pat. No. 3,942,536 of Mirowski et al., the technique involving responses to a sensed peak right ventricular systolic pressure dropping to a fixed predetermined threshold level. This known technique did not involve mean pressure changes in either direction from a baseline. Nor did it involve sensing of pressure within any vessels which extends between the heart and lung(s).

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators (AICD) which is commercially available under the model designations 1500, 1510 and 1520 from Cardiac Pacemakers, Inc. whose address is: 4100 North Hamlin Avenue, St. Paul, Minnesota 55164. These devices continuously monitor myocardial electrical activity, detecting ventricular tachycardia (VT) and ventricular fibrillation (VF), and delivering a shock to the myocardium to terminate the arrhythmia. The AICD has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", Medical Instrumentation, Vol. 20, pages 285-291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", *JACC*, Vol. 6, No. 2, pages 461-466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One problem with current systems is that they function primarily as a rate-only sensing systems and may fire for nonmalignant as well as malignant tachycardias. These firings are not benign; potentially endangering myocardium, wasting energy and inflicting pain on the conscious patient, all distinct shortcomings and disadvantages.

The principal object of the present invention is to provide a system for cardioverting/defibrillating which avoids unnecessary firings, thereby reducing the danger to the myocardium, saving energy and avoiding pain.

Another object of the present invention is to provide an implantable system for cardioverting/defibrillating which avoids unnecessary firings, thereby reducing the danger to the myocardium, saving energy and avoiding pain.

A further object of the present invention is to provide a system for cardioverting/defibrillating which is hemodynamically responsive to change in pressure within at least one vessel (artery or vein) between a heart and lung or lungs of a patient from a baseline.

An additional object of the present invention is to provide a system for cardioverting/defibrillating which is hemodynamically responsive to change in pressure from a baseline and to rate criteria.

Yet another object of the present invention is to provide a method of cardioverting/defibrillating which may be advantageously carried out using a cardioverter-defibrillator constructed in accordance with the present invention.

Yet a further object of the present invention is to provide a method of cardioverting/defibrillating which avoids unnecessary firings thereby reducing the danger to the myocardium, saving energy and avoiding pain.

In accordance with preferred embodiments of the present invention, new sensing algorithms are proposed using hemodynamic or both hemodynamic and rate criteria, the latter being taken in series or parallel. The series configuration algorithm could be effected by detecting rate with an intracardiac, extracardiac, or body-surface R-wave sensor. When rate exceeds the programmed cut-off value, at least one hemodynamic parameter, such as mean pulmonary artery pressure (MPAP), mean pulmonary vein pressure (MPVP), mean pulmonary capillary wedge pressure (MPCWP), mean right atrial pressure (MRAP), mean right ventricular pressure (MRVP), mean central venous pressure (MCVP) or mean arterial pressure (MAP) departures from a baseline would be monitored. Mean left atrial pressure (MLAP) or mean left ventricular pressure (MLVP) may also be suitable as one or another of the hemodynamic baseline parameters from which changes may be monitored. If mean right arterial pressure (MRAP) or mean right ventricular pressure (MRVP) or mean central venous pressure (MCVP) increases from respective baseline MRAP or MRVP or MCVP baselines within a time period of predetermined duration, indicating hemodynamic compromise, the system would fire. If mean left atrial pressure (MLAP) or mean left ventricular pressure (MLVP) increases respectively from respective baseline MLAP or baseline MLVP within a time period of predetermined duration indicating hemodynamic compromise, the system would fire. If mean arterial pressure (MAP) decreases from baseline MAP beyond a predetermined magnitude indicating hemodynamic compromise the system would fire. If the respective pressure changes were less than the respective predetermined magnitudes, pressures would be monitored to determine if respective changes from the respective mean levels take place, as long as the rate criteria is satisfied. The system and method of the invention as disclosed herein may involve mean pulmonary artery pressure (MPAP), mean pulmonary vein pressure (MPVP) or mean pulmonary capillary wedge pressure (MPCWP). A parallel configuration algorithm in which rate and hemodynamic criteria function simultaneously is also proposed; however, continuous pressure change determination would probably be less energy efficient. Either configuration of algorithm could be adapted to a single catheter consisting of a pressure transducer in either the right atrium or right ventricle and an R-wave sensing electrode or pair of electrodes at the catheter tip in the right ventricle. The hemodynamic information derived from an arterial line, Swan-Ganz catheter (already present in the intensive/cardiac care unit patients), or even an automated mechanical blood pressure cuff could be integrated together with the electrocardiogram to provide a temporary automatic antitachycardia system. Cardioversion-defibrillation could be administered using externally applied patches. Even a noninvasive hemodynamically responsive antitachycardia system is potentially feasible using doppler technology for pressure measurements. The PDF (narrow window of function) and the rate/pressure sensing algorithm could be used simultaneously such that if the rate/pressure criteria are satisfied (indicating hemodynamically significant SVT or VT) the device cardioverters and if the PDF criteria is satisfied indicating (VF) defibrillation results. This pulse delivery system could also be incorporated into a single catheter.

It is to be appreciated that when the pressure criteria is not met, but the rate criteria indicates tachycardia is present, an antitachycardia pacemaker could be enabled in an effort to correct the malfunction.

MAP is an excellent parameter but accurate continuous measurement requires an indwelling arterial catheter or transducer which over time is prone to infection and thrombus formation (with the potential for systemic embolic events). Only recently has an extra arterial external wall pressure sensor for chronic arterial pulse pressure sensings been recorded. MRAP and MRVP appear to relate useful information regarding the hemodynamic state of the particular arrhythmia. If tricuspid stenosis were present, MRVP would probably be more reliable than MRAP. Preliminary observations in the canine model suggest that changes as small as 3 mmHg for MRAP and MRVP and as small as 15 mmHg for MAP are significant and can be used in carrying out the present invention.

The rate/pressure sensing algorithms could also help integrate a cardioverter-defibrillator with an antitachycardia pacemaker. The hemodynamic function would determine which of these devices to engage. For example, when a hemodynamically significant tachycardia is detected the cardioverter-defibrillator would be used to terminate the arrhythmia. When a hemodynamically stable tachycardia is sensed the antitachycardia pacemaker would attempt to terminate the arrhythmia using such methods as overdrive, burst, or extra stimulus pacing, incremental or decremental scanning, or ultra-high frequency stimulation. If the tachycardia was accelerated, this would be detected by the rate/pressure sensing algorithm and cardioverted or defibrillated. With a pacemaker present, a bradycardia failsafe could be built into the system.

The adaptation of a hemodynamic parameter to the sensing system of antitachycardia devices appears to be a logical improvement to its present function. MRAP and MRVP are easily measured parameters (via the transvenous route) and appear to relate important hemodynamic information. MAP is an easily measured parameter in the intensive/cardiac care unit setting and could be integrated together with the electrocardiogram to form a temporary automatic antitachycardia system. A long term MPA sensor may be feasible with recent advances. A rate/pressure sensing algorithm, designed either in series or parallel, could be integrated with the PDF system such that hemodynamically significant SVT, VT, and VF would be detected. The rate/pressure sensing algorithm could also be applied to a combined cardioverter-defibrillator and antitachycardia pacemaker.

In its apparatus aspect the invention can be seen as being in a system for treating a malfunctioning heart of the type which includes storage means for storing electrical energy and electrode means for electrically coupling the storage means to the heart. The invention involves pressure responsive sensing means for sensing pressure within at least one vessel (artery or vein) between a heart and at least one lung, means for providing a first signal representative of a fixed or variable baseline pressure and means responsive to output from the sensing means for developing a second signal representing current pressure (such as mean current pressure over a period of given duration). Means respond to output from the means for providing the first signal and output from the means for developing the second signal for charging and enabling discharge of the electrical energy stored by the storage means across the electrode means upon change in the mean current pressure of at least a predetermined amount from the representative fixed or variable baseline pressure.

The pressure responsive sensing means may effect sensing of pulmonary capillary wedge pressure.

In its method aspect, the invention can be viewed as a method of treating a malfunctioning heart which includes sensing pressure within a vessel between the heart and at least one lung and providing a representation of fixed or variable baseline pressure. Current pressure (such as mean current pressure over a period of given duration) is determined from the sensed pressure. Cardioverting/defibrillating electrical energy is delivered to the heart in response to change of at least a predetermined magnitude in the current pressure from the baseline pressure.

The novel features that are considered characteristic of the invention in its method and system aspects are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

BRIEF DESCRIPTION OF THE DRAWINGS

FIG. 2A is an illustration of one catheter positioned within a heart, a pressure responsive sensor forming part of the catheter being shown positioned inside the right ventricle.

FIG. 2B is an illustration of a second catheter positioned within a heart, a pressure responsive sensor forming part of the catheter being shown positioned within the right atrium.

FIG. 2C is an illustration of a third catheter positioned within a major vein feeding into the superior vena cava or in the vena cava itself.

FIG. 2D is an illustration of a fourth catheter positioned within the left side of the heart, a pressure responsive sensor being shown positioned within the left ventricle.

FIG. 2E is an illustration of the fourth catheter positioned within the left side of the heart, a pressure responsive sensor a pressure responsive sensor being shown positioned within the left atrium.

FIG. 2F is an illustration of the fourth catheter positioned within the left side of the heart, a pressure responsive sensor being shown positioned at a point in the arterial system.

FIG. 2H is an illustration of a fifth catheter positioned within the left side of the heart, a pressure responsive sensor being shown positioned within a pulmonary artery between the heart and at least one lung.

FIG. 2I is an illustration of a sixth catheter positioned within the left side of the heart, a pressure responsive sensor being positioned with a pulmonary vein between at least one lung and the heart.

FIG. 2J is an illustration of a fifth catheter positioned within the left side of the heart, a pressure responsive sensor being positioned to effect sensing of pulmonary capillary wedge pressure.

DETAILED DESCRIPTION OF THE PREFERRED EMBODIMENTS

Figure 1:
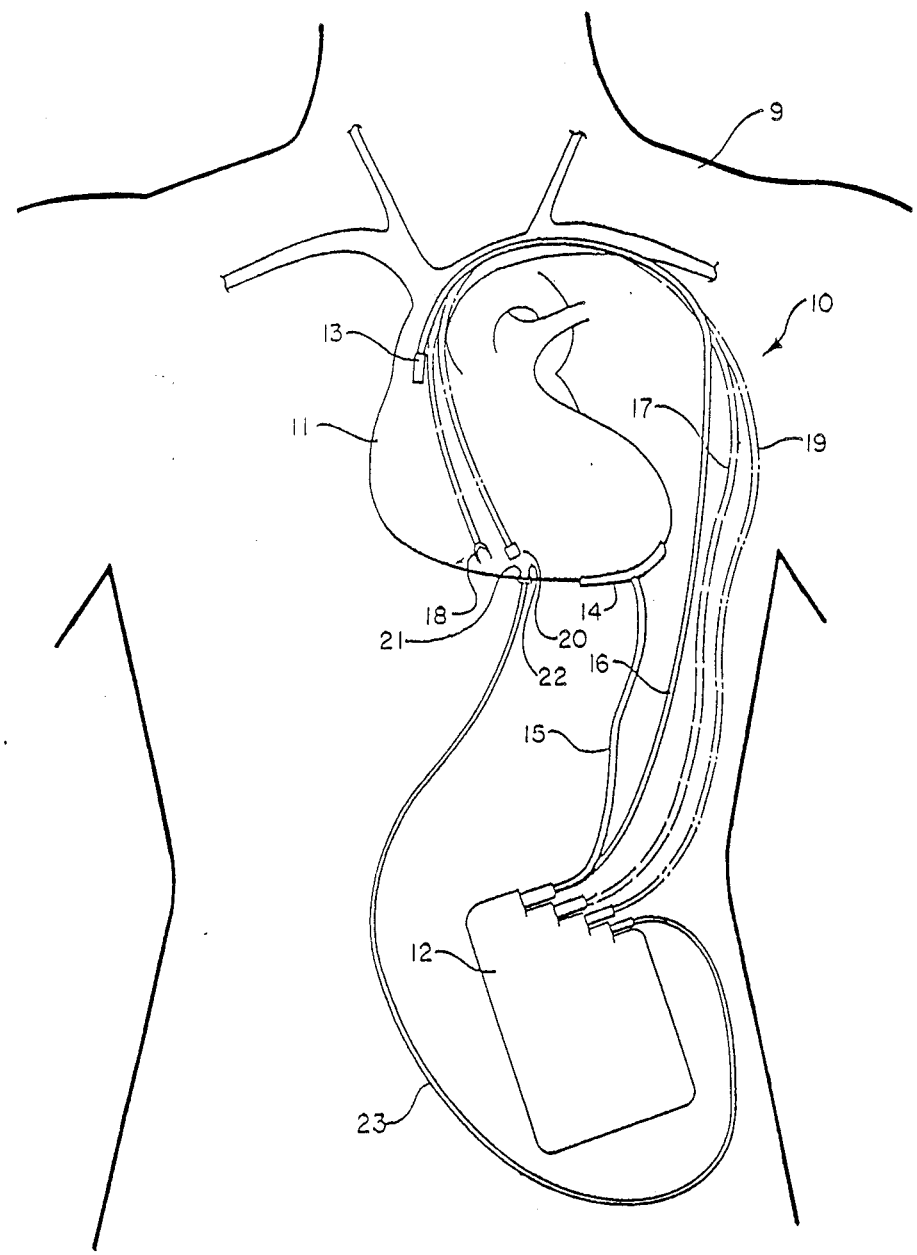
FIG. 1 is a diagrammatic, generalized illustration of an exemplary, implanted hemodynamically responsive system for treating a malfunctioning heart.

As shown in FIG. 1, an exemplary embodiment of an automatic implantable cardioverter-defibrillator system is designated generally by the numeral 10 and illustrated diagrammatically as being implanted within a human subject 9. The cardioverter-defibrillator system 10 includes an implanted housing 12 within which major circuit components of the system are housed. A first electrode 13 is positioned within the heart 11 of the subject 9, the details of placement and nature of the first electrode being more specifically shown in FIGS. 2A–2F and 2H–2J to which reference is to be made below. A second electrode, illustrated as a patch electrode 14 is positioned on the outside of the heart 11 at the apex thereof. The pair of electrodes 13, 14 are provided for the purpose of delivering D.C. cardioverting-/defibrillating energy from within the housing 12 to the heart 11 under control of circuitry within the housing, a pair of insulated leads 16 and 15 respectively being provided for this purpose. A pair of rate sensing electrodes 18 are provided within the heart 11, these electrodes being positioned in tissue and being conductively coupled to circuitry within the housing 12 via an insulated cable 17. A further pair of leads extend from a pressure responsive pressure-to-voltage transducer 20 to circuitry within the housing 12 via an insulated cable 19. It is to be understood that the insulated leads 15 and 16, the insulated cable 17 (or the pair of leads therein), and the insulated cable 19 (or the pair of leads therein) can all be incorporated into a single cable, the electrode 13, the rate sensing electrodes 18 and the pressure transducer 20 being carried by and forming parts of a catheter.

Pacemaking circuitry within the housing 12 may be provided to produce antitachycardia pacemaking signals, to a pair of pacing electrodes 21 and 22, illustrated as being fixed in tissue on the right-side of the heart. The pacing electrodes 21 and 22 are connected by respective conductive leads within a cable 23 which communicates with circuitry within the housing 12.

Turning to FIG. 2A, a more detailed illustration of the heart 11 of a subject, shows the heart in somewhat more detail and in section so that placement of parts of the system within the heart 11 can be seen in more detail, albeit diagrammatically. The heart 11 as illustrated includes a right ventricle 26, a right atrium 27, a left atrium 28 and a left ventricle 30. The electrode 13 is positioned within the superior vena cava. It is to be understood that the patch electrode 14, which cooperates with the electrode 13, could also be modified into a different form so it too could be positioned within the heart. The electrode 13 could be replaced with a patch electrode so that it also could be positioned on the surface of the heart, without departing from the present invention. The electrodes 13 and 14, in cases not involving implantation, could be replaced with conventional paddle electrodes or other external, body engaging electrodes, again without departing from the present invention. Thus, the invention could be used as a temporary measure for patient care in intensive care units and the like.

As illustrated in FIG. 2A, the pacing electrodes 21 and 22 are shown as being positioned on the exterior wall of right ventricle 26 for the purpose of illustration; these pacing electrodes could be placed elsewhere on or within the heart 11 in accordance with the needs of individual patients, taking into account the best particular location most suitable for correcting or overcoming the particular malfunction involved, the condition of the individual patient and his or her heart being taken into account.

Heart rate wave (R-wave) sensing electrodes 18a and 18b are illustrated as being positioned near the apex of the heart 11 within the right ventricle 26, for purposes of illustration. Other locations are equally well suited; again, the selected location being chosen with the condition of the particular patient and his or her heart in mind. The electrodes 18a and 18b are conductively connected to the circuitry within the housing 12 via leads 17a and 17b within the cable 17.

The pressure-to-voltage transducer 20, as illustrated in FIG. 2A, is positioned within the right ventricle 26. Two conductive leads 19a and 19b within the cable 19 (FIG. 1) provide electrical communication from the pressure responsive transducer 20 to circuitry within the housing 12 (FIG. 1). Thus, a D.C. voltage signal representative of the actual, instant pressure within the right ventricle 26 is fed to the circuitry within the implanted housing 12 (FIG. 1).

As illustrated in FIGS. 2B-2F and 2H-2J the heart 11, as well as the components of the system of the present invention, other than the pressure-to-voltage transducer 20 (or 20'), correspond to the heart 11 and the system components as shown in FIG. 2A. The placement of the transducer 20 (or 20') differs, in each of FIGS. 2B-2F and 2H-2J. As shown in FIG. 2A, the transducer 20 (or 20') provides, as its output, a variable D.C. voltage representative of the varying pressure within the right ventricle 26. As shown respectively in FIGS. 2B-2F and 2H-2J, the transducer 20 is positioned within and produces a variable D.C. voltage which represents respectively the pressure within the right atrium 27, within the central venous system (in particular, a major vein 29) the left ventricle 30, the left atrium 28, the arterial system (in particular, an artery 31 remote from the heart 11), a pulmonary artery, a pulmonary vein and a point to sense pulmonary capillary wedge pressure.

In FIG. 2H, a fifth catheter is shown positioned in the right side of the heart. A pressure responsive sensor 20, in this case, is positioned in one of the pulmonary arteries extending toward one of the lungs. The sensor 20 could, if desired, be positioned more upstream in the large pulmonary artery which carries blood to both lungs. The sensor 20 could be positioned in one of the smaller arteries which carries blood to one or another of the lobes of one lung. The other, components of the catheter fifth correspond to those illustrated in FIGS. 2A-2C.

It is also within the contemplation of the present invention to place the pressure sensor 20 within a pulmonary vein (feeding into left side of heart), as shown diagrammatically in FIG. 2I; in this case the conductive leads 19a, 19b and the cable 19 are positioned in the vicinity of the vein, with the leads 19a and 19b extending through the wall of the vein. In this case, the other components of the sixth catheter correspond to those of the catheters shown in FIGS. 2D-2F.

Referring to FIG. 2J, a sensor 20' is shown positioned within a small blood vessel (being fed from a minor pulmonary artery) for the purpose of measuring pulmonary capillary wedge pressure. In a realized study conducted by applicant, pulmonary capillary wedge pressure was sensed using a dual lumen transvenous ballon tip catheter which was placed into the right heart chambers through the internal jugular vein and, thence, into the blood vessel. The other components of the catheter shown in FIG. 2J correspond to those shown in FIGS. 2H and 2I.

Figure 2G:
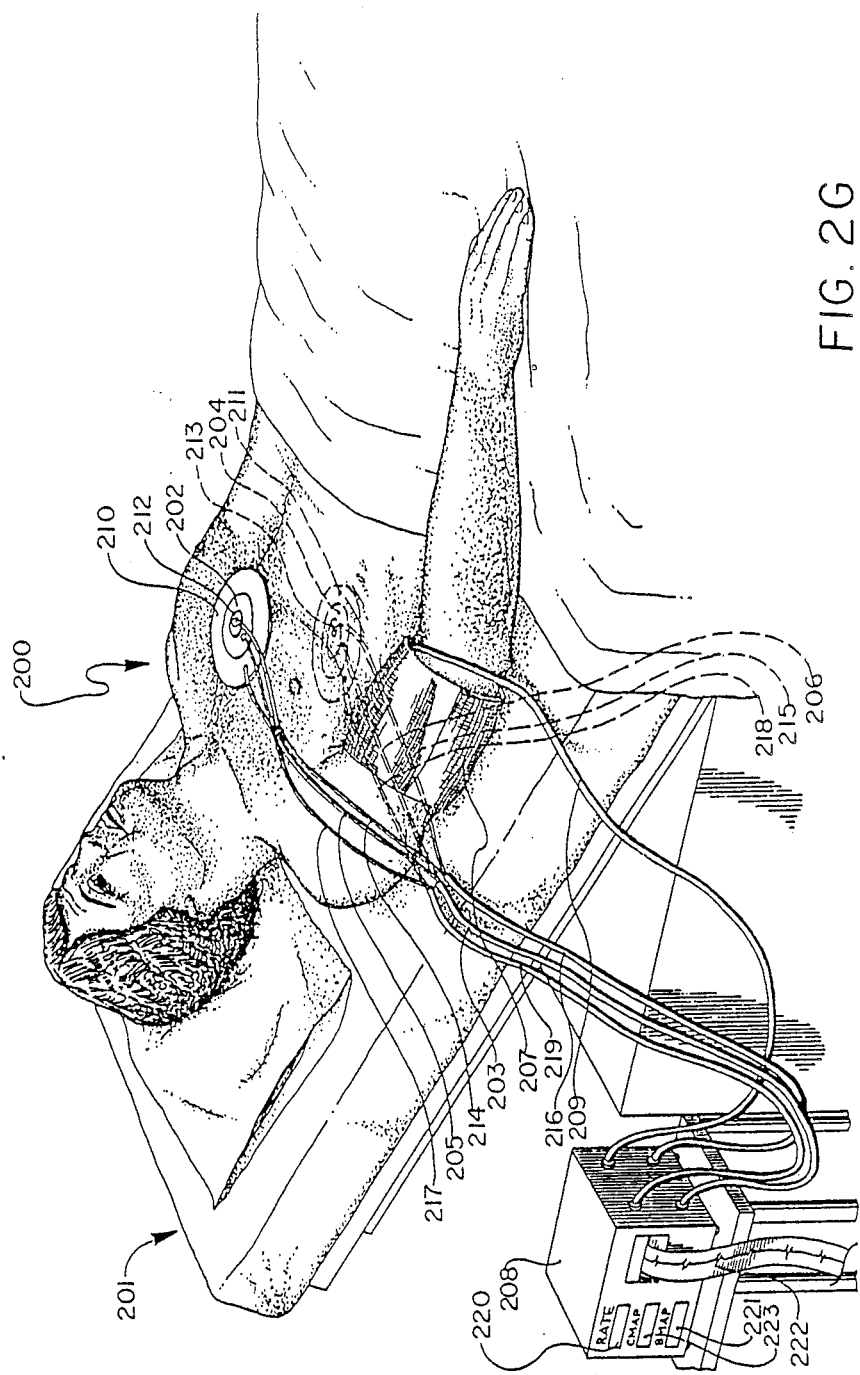
FIG. 2G is an illustration of a variant in which an external blood pressure cuff is provided to sense arterial pressure, from which MAP can be derived.

In FIG. 2G a portion of a noninvasive system for sensing heart rate and pressure of the type which may be used in an intensive care unit (ICU), a recovery room, coronary care unit (CCU), and/or in a routine care patient facility is illustrated. The system of FIG. 2G can be considered a system which can be substituted for the invasive systems shown in FIGS. 1, 2A-2F and 2H-2J. A patient 200 is shown in a reclined posture on a bed 201. A pair of pulse-delivering electrodes 202 and 204 (substitutes for electrodes 13, 14; FIGS. 2A-2F and 2H-2J) are positioned respectively on the anterior and posterior chest of the patient 200 for the purpose of coupling cardioverting/defibrillation energy pulses to the patient, respective insulated leads 205 and 206 (substitutes for leads 15, 16; FIGS. 2A-2F and 2H-2J) and a cable 203 being provided to conduct the pulses to the patient, from a pulse-generating apparatus 208 (substitute for the circuitry within housing 12; FIG. 1). The leads 205 and 206 and electrodes 202 and 204 are to be used in place of the cardioverting/defibrillating electrodes 13 and 14 (FIGS. 1, 2A-2F and 2H-2J), were the system of the present invention to be used in a noninvasive stand-alone or portable or patient-carried configuration, instead of in an implantable configuration as illustrated in FIGS. 1, 2A-2F and 2H-2J. Positioned concentrically about the respective electrodes 202 and 204 and insulated therefrom, are respective pacing electrodes 210 and 211 (substitutes for 21, 22; (FIGS. 1, 2A-2F and 2H-2J). A pair of respective rate (R-wave) sensing electrodes 212 and 213 (substitutes for electrodes 18, FIG. 1; 18a, 18b, FIGS. 2A-2F and 2H-2J) are provided centrally within and insulated from the electrodes 202 and 204, respectively. The pair of rate-sensing electrodes 212, 213 are connected respectively via respective insulated leads 214, 215 and a cable 216 to the apparatus 208. The pair of pacing electrodes 210, 211 are connected respectively via respective insulated leads 217, 218 and a cable 219 to the apparatus 208.

Moreover, rather than an invasive pressure transducer of the type illustrated in FIGS. 1, 2A-2F and 2H-2J, the system may be modified to sense, in a noninvasive fashion, arterial pressure using a conventional cuff 207 removably fixed to, as shown, the right upper arm of the patient 200, the sensed pressure-related electrical signals being produced by a conventional transducer within the apparatus 207. A pneumatic tube or conduit 209 is provided both to supply automatically and intermittently compressed air to the cuff 207 and to receive either audible sounds (which are processed within the apparatus 208 to derive MAP representing data) or an electrical output from a transducer positioned within the cuff 207. The transducer produces electrical output signals which appears on a pair of conductive leads within the conduit 209. The cuff 207 is supplied, as is conventional, intermittently with compressed air via the air conduit 209. The components illustrated in FIG. 2G are used to monitor arterial blood pressure intermittently, for example once for a short period every 30 seconds. The pressure data so developed can be used to develop long-term mean baseline pressure-related signals and short-term (current) mean pressure-related signals. Such intermittently developed inputs can, as will be readily understandable by persons skilled in the art, be used in place of the inputs provided from the pressure sensing transducer 20 or 20' (FIGS. 1, 2A-2F and 2H-2J) to derive pressure- and heart rate-representing input signals for use in conjunction with the circuits discussed hereinbelow. The apparatus 208 may be provided with a heart rate display 220, baseline MAP display 221, and a current MAP display 223. An EKG strip recording 222 could be produced by the apparatus from a connection electrode arrangement (now shown) which could include the rate (R-wave) sensing electrodes 212 and 213.

Figure 3:
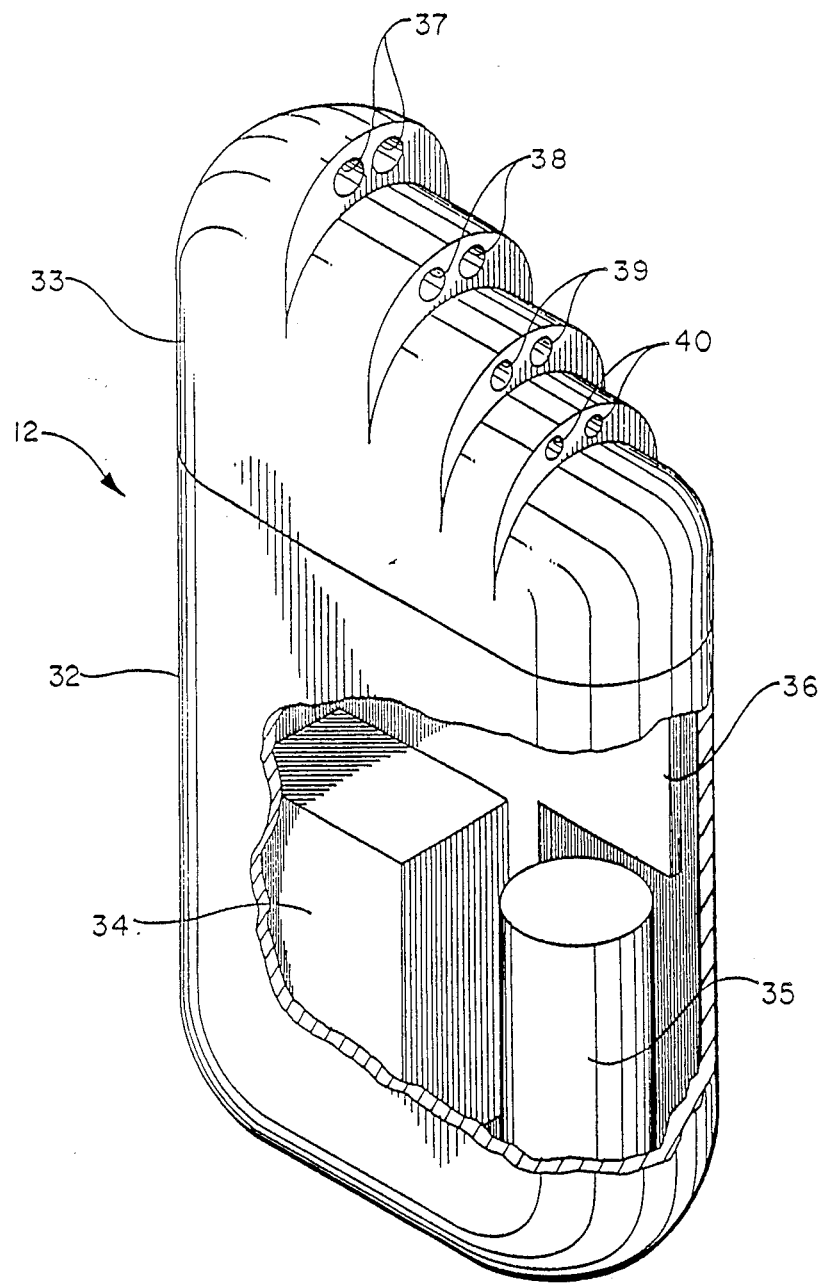
FIG. 3 is a pictorial illustration of an exemplary implantable controllable cardioverting/defibrillating electrical energy generator which may be used in practicing the present invention, the housing of the generator being partially broken away to show positioning of major components thereof.

One possible general implantable configuration of the housing 12 is shown in FIG. 3. The housing 12 includes a case 32, made of titanium, and a header 33, formed of an epoxy material, fixed to the case 32, all external components being hermetically sealed and biocompatible for human implantation. Within the case 32 is a battery pack or battery 34, an energy storage capacitor 35 and an electronic module 36 in or on which circuit components, other than the battery pack or battery 34 and the capacitor 35, are positioned. Detailed embodiments of exemplary circuits which are in or on or connected to the module 36 are illustrated in FIGS. 4, 6, 8 and 10, to which reference is made hereinbelow. A plurality of pairs of receptacles 37-40 are shown in the header 33 for receiving corresponding pairs of leads which are respectively within the insulated cables 15, 16 and 17 and 19 and 23 (FIG. 1).

Figure 4:
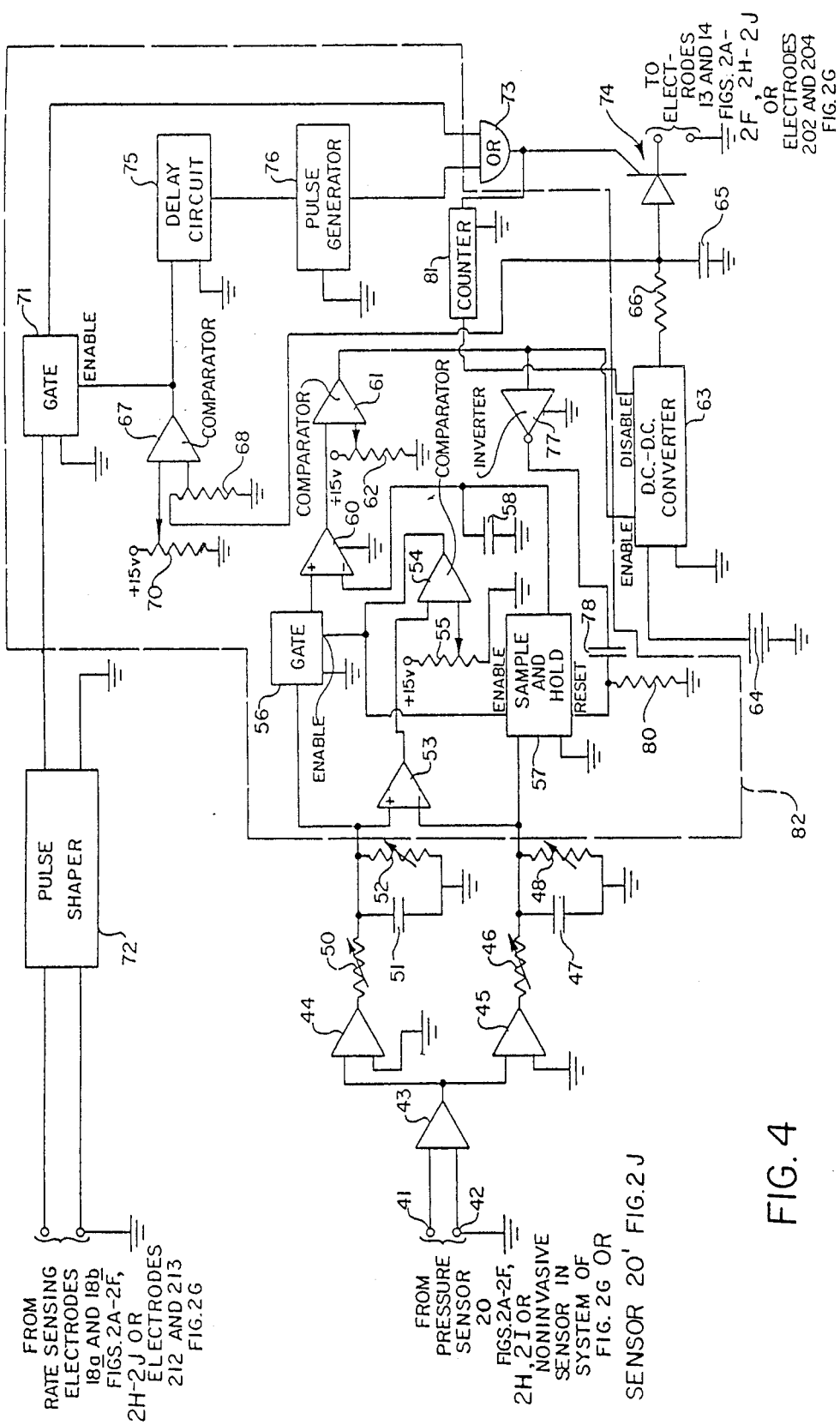
FIG. 4 is a partially block, schematic diagram of a hemodynamically responsive system for treating a malfunctioning heart which is pressure responsive.

Turning to FIG. 4, an exemplary embodiment of the circuit components, which may be positioned within the housing 12 (FIGS. and 3) or the bed-side apparatus 208 (FIG. 2G), includes a pair of input terminals 41, 42 which receive the variable D.C. voltage output signal representing pressure from the pressure responsive transducer 20 or 20' (FIGS. 1, 2A-2F and 2H-2J) or noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 4 is suitable for treating a malfunction heart using a pressure-only criteria.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage across the capacitor 47 represents the mean pressure sensed by the transducer 20 or 20' (FIGS. 1, 2A-2F and 2H-2J) or a noninvasive transducer (in system of FIG. 2G) over a relatively long period, for example during the preceding fifteen (15) minutes or even longer (for example a number of hours) or shorter (for example one hundred twenty (120) seconds) being suitable in some cases. The resistors 46 and 48 may be set by a medical professional to suit the particular patient involved, so far as what the most suitable period length (period of predetermined length) for baseline data acquisition appears to be most suitable. The D.C. voltage (first signal) which appears across the capacitor 47 thus represents a long term mean baseline pressure. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 or 20' (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds). The resistors 50 and 52 may be set by a medical professional to suit the particular patient involved, so far as what the most suitable period length (period of given length) for current data acquisition appears to be most suitable.

As illustrated the long term (baseline) and short term (current) D.C. voltage signals which appear across the respective capacitors 47 and 51 are fed respectively to the inverting and noninverting terminals of an operational amplifier 53, a difference D.C. voltage signal appearing as the output from the operational amplifier 53. As shown, the inverting and noninverting terminals of the operational amplifier 53 are connected as they would be were pressures other than arterial pressures to be involved. Were MAP to be the hemodynamic parameter involved, the terminals would be reversed. The D.C. output signal from the operational amplifier 53 is fed to a first input terminal of a first comparator 54, the second input terminal of the comparator 54 is connected to the wiper of a potentiometer 55 which is connected between ground and a point of fixed D.C. potential, illustrated as being +15 volts, from an internal power supply bus.

Whenever the voltage supplied to the comparator 54 from the operational amplifier 53 exceeds the voltage supplied via the wiper from the potentiometer 55, a low (ZERO) level on the output terminal from the comparator 54 goes high (ONE), the ONE signal being coupled as an enabling input to a gate 56 and to a sample-and-hold circuit 57 which receive, at their respective signal input terminals, the voltage representing current mean pressure appearing across the capacitor 51 and the voltage representing mean baseline pressure appearing across the capacitor 47.

A D.C. output from the sample-and-hold circuit 57 is stored in a storage circuit, for the purpose of illustration shown as a capacitor 58. This stored voltage signal (stored first signal) representing mean baseline (long-term) pressure is supplied to the inverting input terminal of an operational amplifier 60 which has its noninverting input terminal connected to the output terminal of the gate 56, which when enabled, passes the D.C. voltage signal appearing across the capacitor 51 and representing current (short-term) mean pressure to the operational amplifier 60. As illustrated, the inverting and noninverting terminals of the operational amplifier 60 are shown as they would be connected were pressures other than arterial pressure involved. Were MAP to be the hemodynamic parameter selected, the terminals would be reversed. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. It is to be understood that the wipers of the potentiometers 55 and 62 are independently adjustable; consequently, the wiper on the potentiometer 62 may be positioned so that the pressure difference which causes its output to go from ZERO to ONE is slightly greater than pressure difference which causes the comparator 54 to initiate the enabling functions. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse is a truncated exponential pulse of about 25 Joules delivered approximately 17 seconds from onset of the hemodynamic compromise. The pulse could, especially when defibrillation is being undertaken after a failed attempt to cardiovert, be delivered somewhat later and with a higher energy level.

Once the capacitor 65 is charged to a sufficiently high D.C. voltage level to provide sufficient energy to effect cardioversion, as determined by a comparator 67, which receives on one input terminal a voltage proportional to the increasing D.C. voltage across the capacitor 65, a highly resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or from the rate sensing electrodes 212, 213 (FIG. 2G) and produces a pulse train in synchronism with the R-wave supplied from the electrodes 18a, 18b or electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy then stored on the capacitor 65 into the malfunctioning heart, via the electrodes 13 and 14 (FIGS. 1, 2A-2F and 2H-2J) or the electrodes 202 and 204 (FIG. 2G) in an effort to effect cardioversion, the discharge being in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more and enables a pulse generator 76 causing it to produce an output pulse to initiate defibrillation which is supplied, via the OR circuit 73, to the gate electrode of the SCR 74 causing the SCR to fire. The energy storage capacitor 65, which by then has charged to a higher level discharges, via the SCR 74 and the electrodes 13 and 14 (FIGS. 1, 2A-2F and 2H-2J) or the electrodes 202 and 204 (FIG. 2G), into the malfunctioning heart in an effort to effect defibrillation, the energy level being higher than would have been the case had the capacitor been discharged three seconds earlier. The delay circuit may be composed of an RC circuit connected to the comparator 67 so that the capacitor thereof charges toward the ONE level slowly; for example the capacitor may take about three (3) seconds or more as indicated above to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the stored signal representing baseline mean pressure and the signal representing current mean pressure returns to an acceptable level, indicating that the hemodynamic compromise has been overcome. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure (which would cause the output of the comparators 54 and 61 to become ZERO, removing the enable signals from the sample-and-hold circuit 57 and the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. An internal timer within the converter 63 holds the converter OFF for a given period so that the patient will not receive more shocks during this given period. At the end of the period the converter 63 returns to a READY condition and is again able to respond to an ENABLE signal from the comparator 61. The counter 81 resets itself to zero whenever it either reaches its maximum count of four or fails to reach the count of four within the given time period.

Figure 5A:
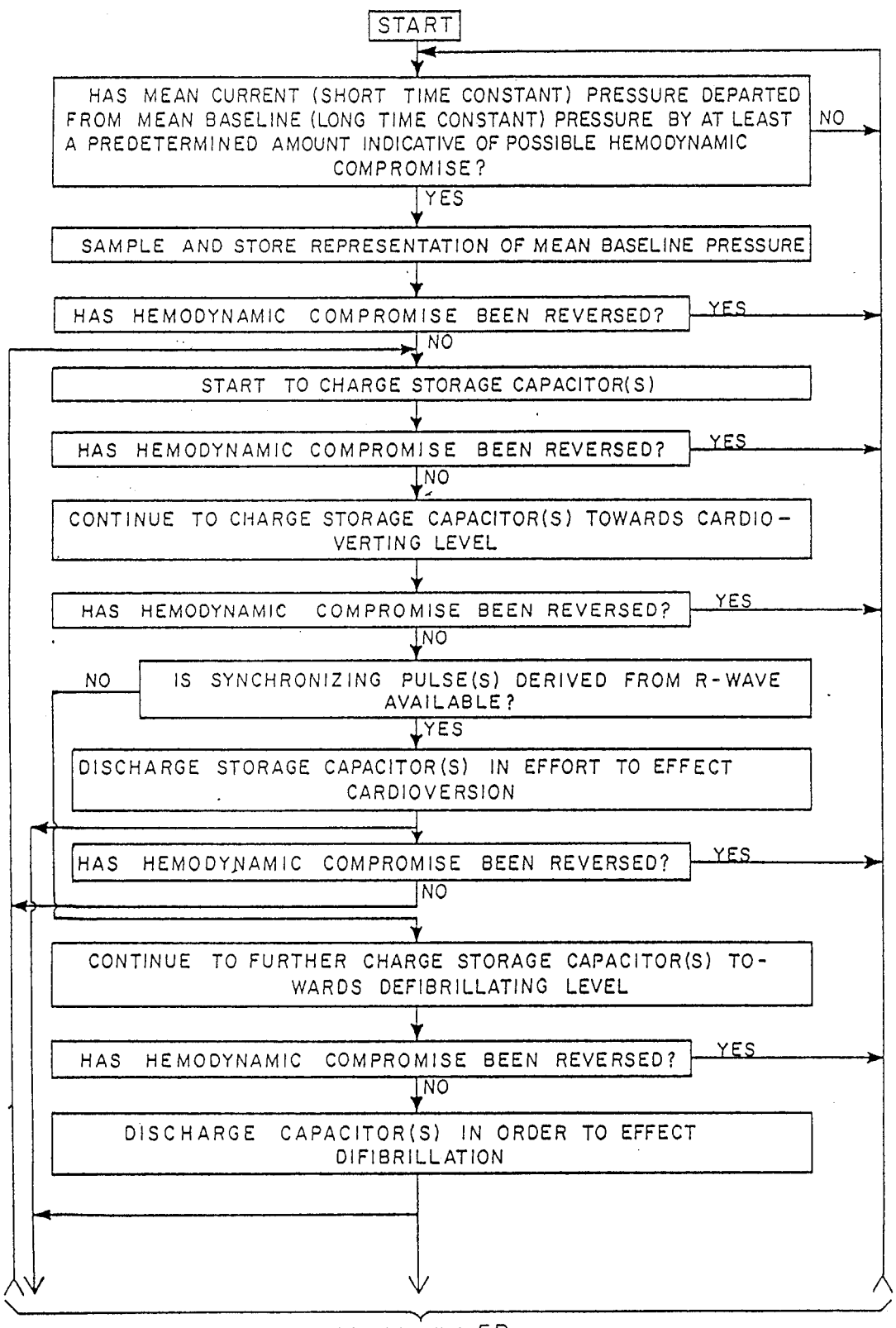
FIGS. 5A and 5B constitute a first exemplary flowchart of a series of actions or steps which may be carried out by the system illustrated in FIG. 4 and effect achievement of a corresponding method.
Figure 5B:
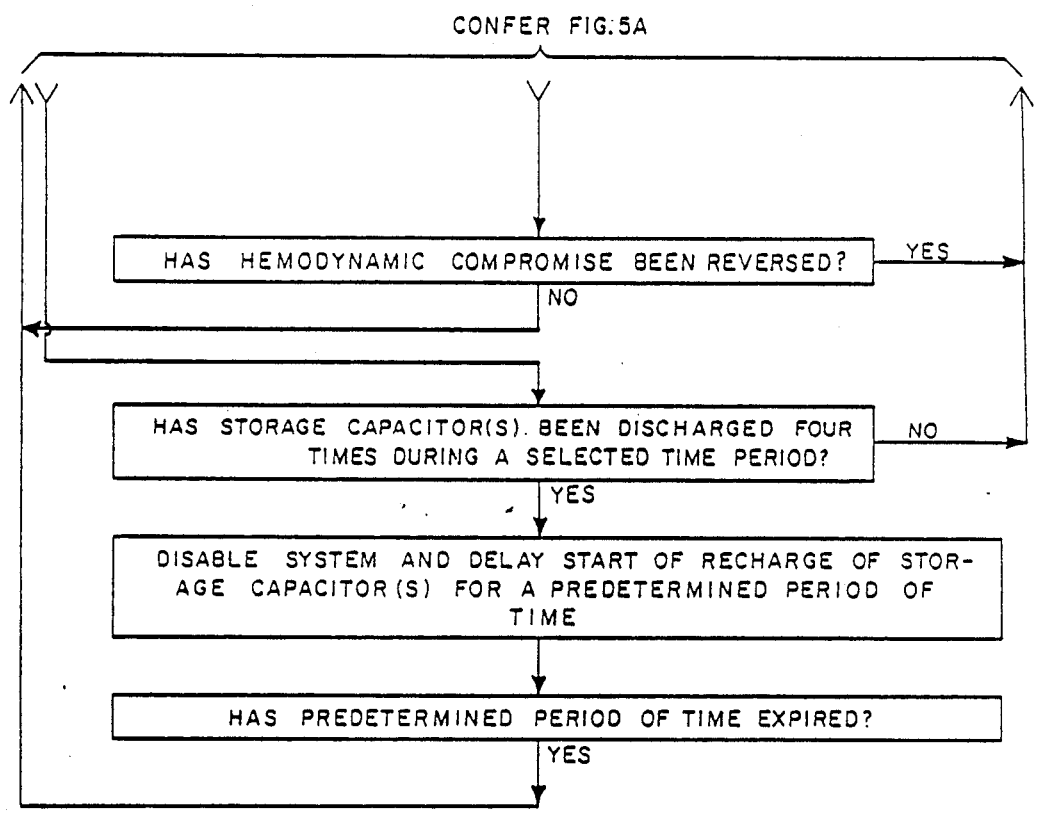

It is to be appreciated that the circuit of FIG. 4 described above may be considered, at least in part, to be a controller or processor, which could be realized as a microprocessor, the processor being identified by the numeral 82. The processor 82, with its associated components, in effect carries out the steps set out in the flowchart of FIGS. 5A and 5B.

The circuit of FIG. 4 could be associated with an antitachycardia pacemaker and/or an antibradycardia pacemaker, if desired.

Figure 6:
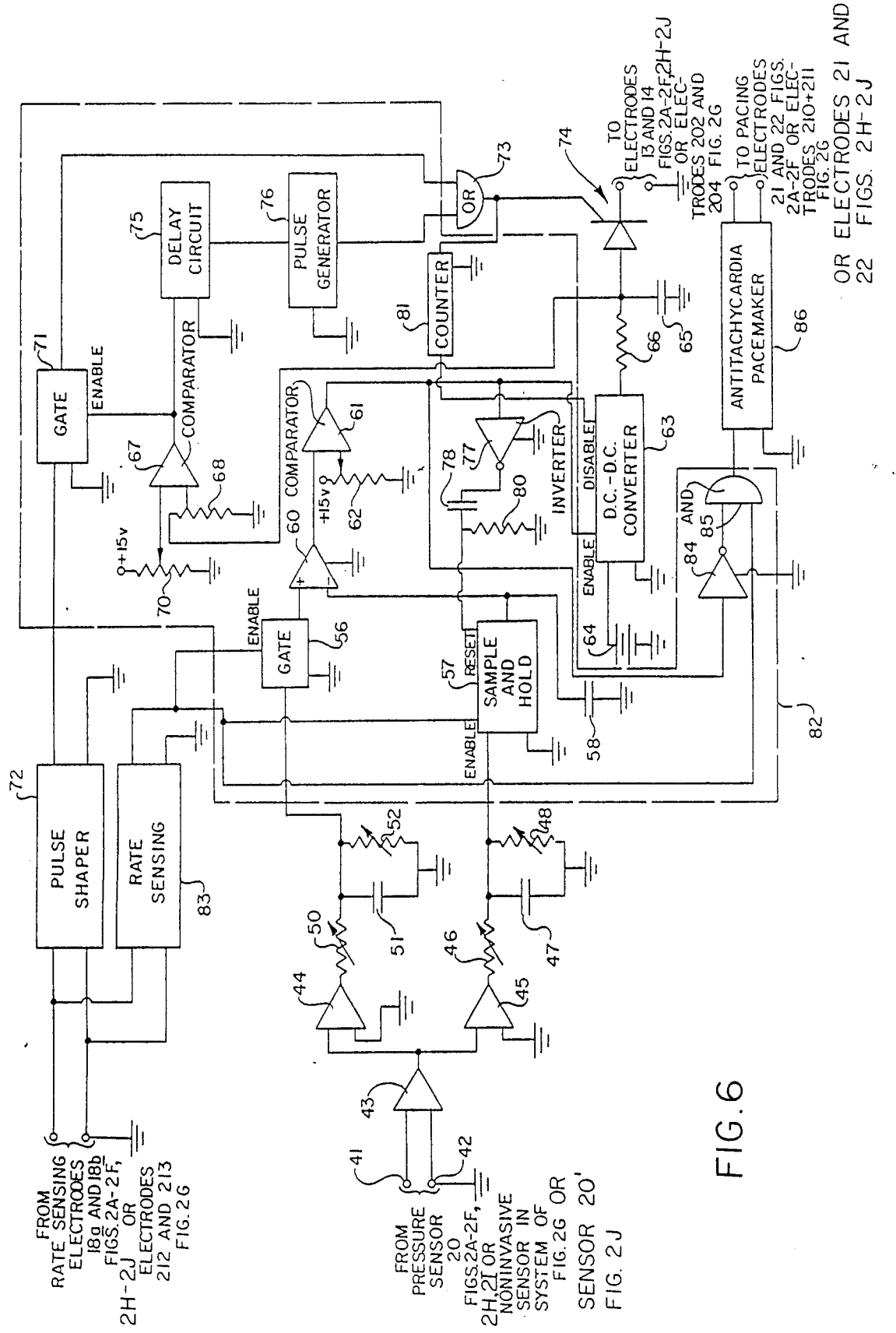
FIG. 6 is a partially block, schematic diagram of a further hemodynamically responsive system for treating a malfunctioning heart which is pressure and rate responsive.

Turning to FIG. 6, a further exemplary embodiment of the circuit components, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 or 20' (FIGS. 1, 2A-2F and 2H-2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 6, with associated components, is suitable for practicing the present invention in which both pressure and beating rate criteria are to be taken into account. The rate criterion is examined first and, if met, the pressure criteria are then considered.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage (first signal) across the capacitor 47 represents the mean pressure sensed by the transducer 20 or 20' (FIGS. 1, 2A-2F and 2H-2J) or the noninvasive transducer (in system of FIG. 2G) over a relatively long period, for example during the preceding fifteen (15) minutes or even longer (for example a number of hours) or shorter (for example one hundred twenty (120) seconds) being suitable in some cases. The D.C. voltage (first signal) which appears across the capacitor 47, thus represents a long term mean baseline pressure. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 or 20' (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to the signal input terminal of a sample-and-hold circuit 57 and to the signal input terminal of a gate 56. A rate sensing circuit 83 is arranged to receive a beating rate (R-wave) signal from the rate sensing electrodes 18a, 18b (FIGS. 1, 2A-2F and 2H-2J) or from the rate sensing electrodes 212, 213 (FIG. 2G). Whenever the rate exceeds a given rate, for example 155 beats per minute, indicating tachycardia, the output terminal of the rate sensing circuit 83 goes from low (ZERO) to high (ONE). The ONE signal (first control signal) is supplied as an enabling input to the gate 56 and to sample-and-hold circuit 57. The D.C. voltage representing current mean pressure appearing across the capacitor 51 is fed via the enabled gate 56 to the noninverting input terminal of an operational amplifier 60. The D.C. voltage representing mean baseline pressure appearing across the capacitor 47 is transferred to the sample-and-hold circuit 57, appearing across its associated capacitor 58. This stored D.C. voltage representing mean baseline pressure is supplied to the inverting input terminal of the operational amplifier 60 which has its noninverting input terminal connected to the output terminal of the gate 56 which, when enabled as noted above, passes the D.C. voltage signal appearing across the capacitor 51 and representing current mean pressure to the operational amplifier 60. As illustrated, the input terminals of the operational amplifier are connected as they would be to receive signals other than arterial pressure. Were MAP to be the selected hemodynamic parameter, the terminals would be reversed.

The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) and the signal (second control signal) is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting-/defibrillation pulses. The desired pulse for cardioversion is a truncated exponential pulse of about 25 Joules delivered approximately 17 seconds from onset of the hemodynamic compromise.

Once the capacitor 65 is charged to a sufficiently high D.C. voltage level to provide sufficient energy to effect cardioversion, as determined by a comparator 67, which receives on one input terminal a voltage proportional to the instant D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or from the rate sensing electrodes 212, 213 (FIG. 2G) and produces a pulse train in synchronism with the R-wave supplied from the electrodes 18a, 18b or from the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A-2F and 2H-2J) or the electrodes 202, 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce output pulse to initiate defibrillation. The pulse is supplied, via the OR circuit 73, to the gate electrode of the SCR 74 causing the SCR to fire. The energy storage capacitor 65, which during the elapsed three seconds has charged to a higher level, discharges, via the SCR 74 and the electrodes 13 and 14 (FIGS. 1, 2A-2F and 2H-2J) or electrodes 202 and 204 (FIG. 2G), into the malfunctioning heart via the electrodes 13 and 14 (FIGS. 1, 2A-2F and 2H-2J) or electrodes 202 and 204 (FIG. 2G) in an effort to effect defibrillation, the energy level being higher than it would had been had discharge been effected three (3) or more seconds earlier. The delay circuit may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean pressure and current mean pressure returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure by overcoming the hemodynamic compromise (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to ZERO count whenever it either reaches its maximum count of four or fails to reach the count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 6, cardioverting/defibrillating D.C. pulses are delivered to the malfunctioning heart only when the rate criterion is first satisfied and, thereafter, the pressure criteria also satisfied. This can be viewed as a series rate-pressure algorithm.

In the event the rate criterion is met, but the pressure criteria are not; that is to say no hemodynamic compromise presents, the circuit of FIG. 6 nevertheless acts to enable an antitachycardia pacemaker 86 which supplies pacing signals to the pair of pacing electrodes 21, 22 (FIGS. 1, 2A-2F and 2H-2J) or the pair of pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs to the AND circuit 85 are ONE, the antitachycardia pacemaker 86, which may be any one of a number of conventional types is energized.

Figure 7A:
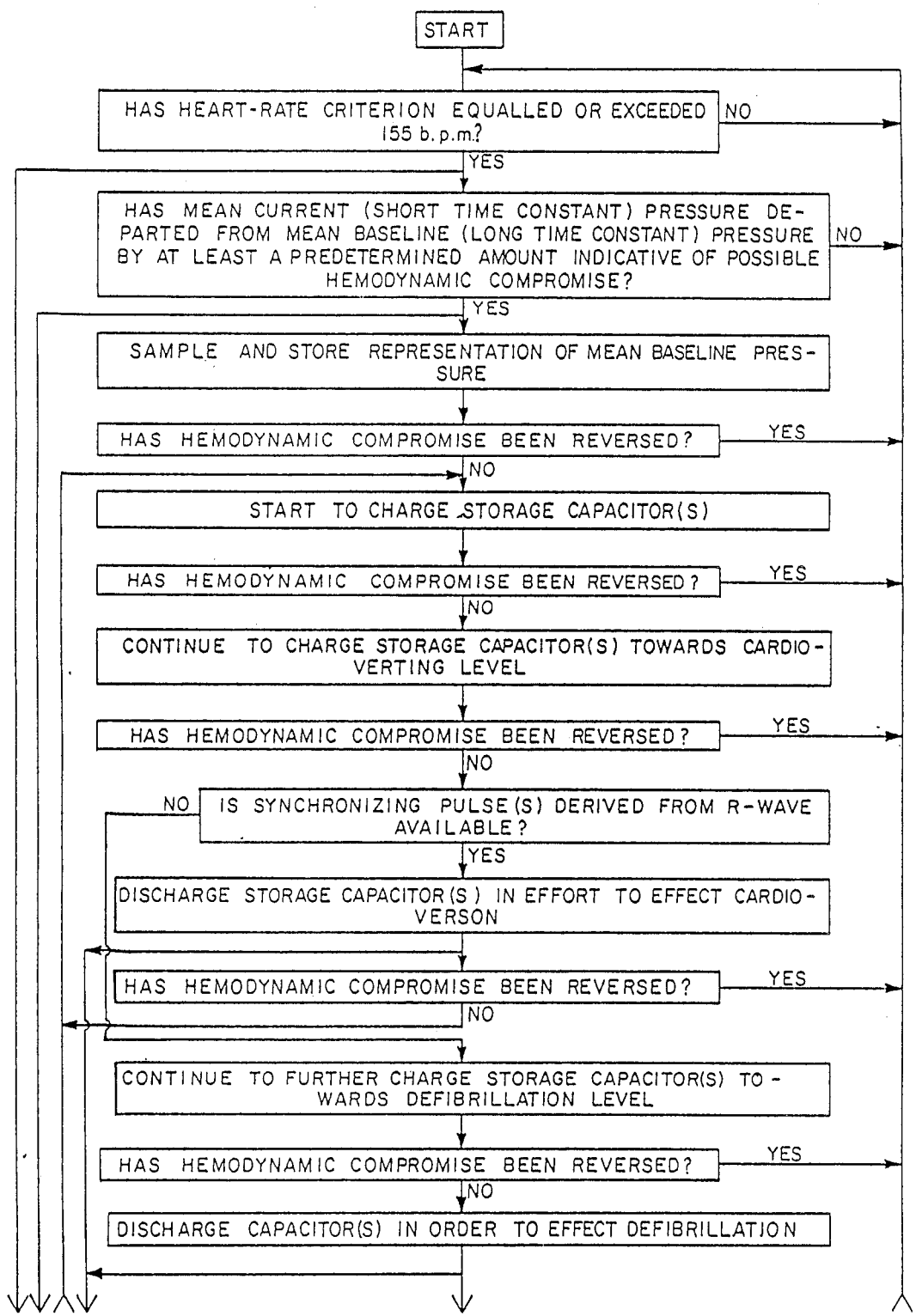
FIGS. 7A and 7B constitute a second exemplary flowchart of a series of actions or steps which may be carried out by the system illustrated in FIG. 6 and effect achievement of a corresponding method.
Figure 7B:
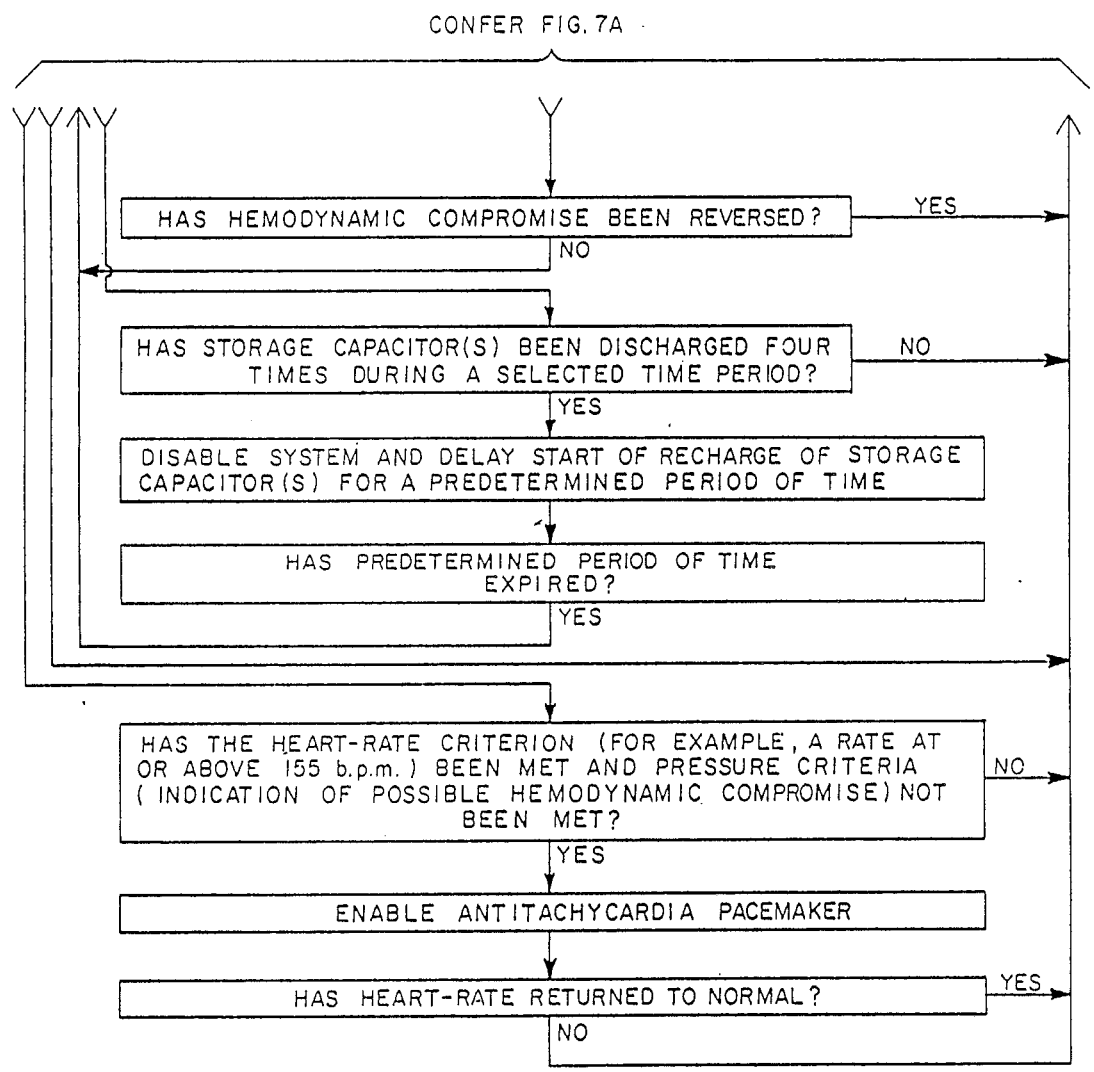

It is to be appreciated that the circuit of FIG. 6 described above may be considered, at least in part, to be a processor, which could be realized as a microprocessor, the processor being identified by the numeral 82. The processor 82, with its associated components, in effect carries out the steps set out in the flowchart of FIGS. 7A and 7B.

It is to be understood that the system of FIG. 6 could be associated with a failsafe antibradycardia pacing system, if desired.

Figure 8:
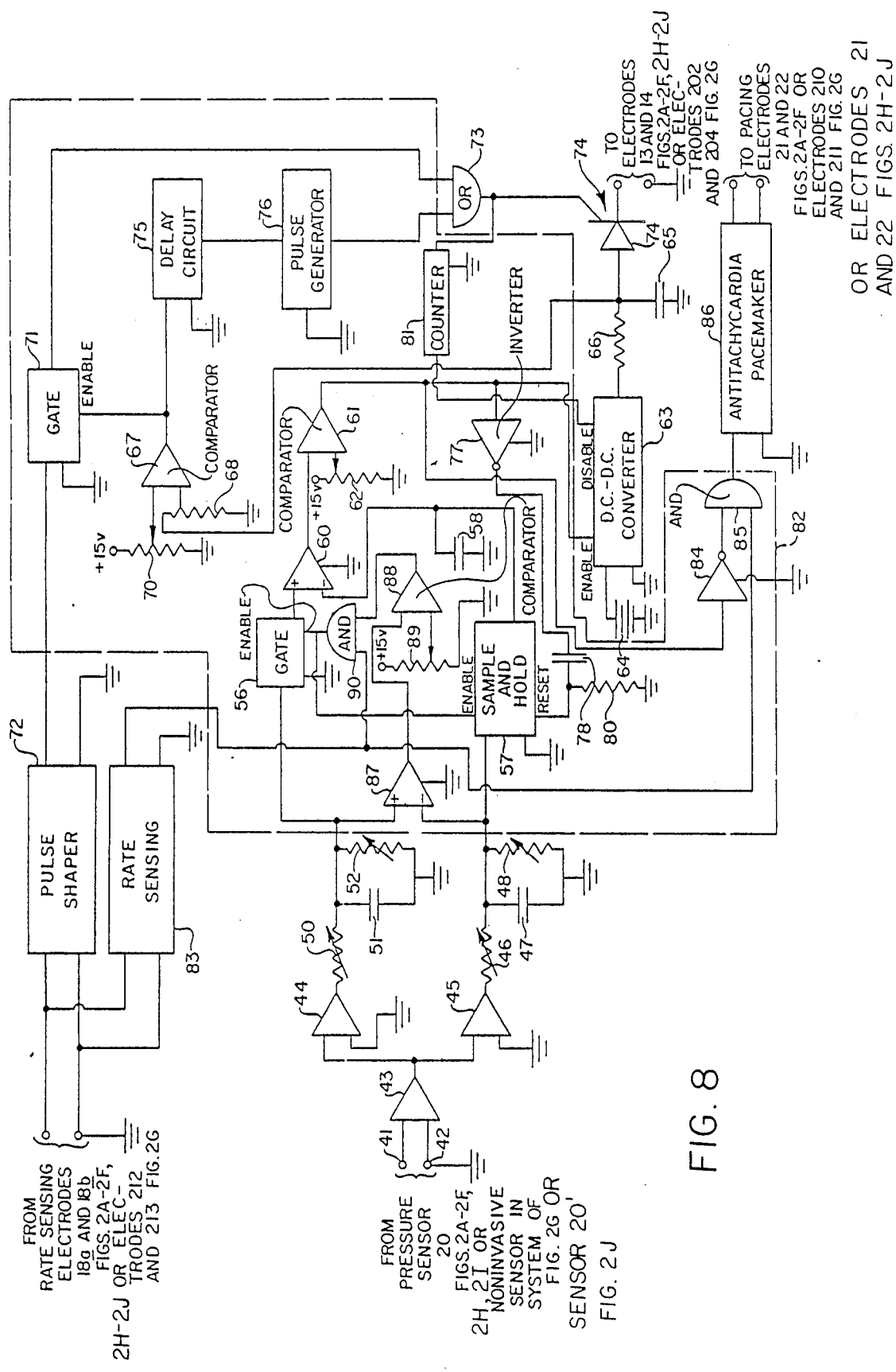
FIG. 8 is a partially block, schematic diagram of hemodynamically responsive system for treating a malfunctioning heart which is a variant of the circuit of FIG. 6.

Turning to FIG. 8, an additional exemplary embodiment of the circuit components, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 or 20' (FIGS. 1, 2A-2F and 2H-2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 8 can be used in practicing the present invention using both rate and pressure criteria. In this case the rate and pressure criteria must exist simultaneously to start the sample-and-hold function.

The output from the buffer amplifier 45 is supplied to an RC circuit constituted by an adjustable resistor 46 connected to ground via a series connected capacitor 47 having a large adjustable resistor 48 connected in parallel therewith. The time constants (charging and discharging) of these circuit components are such that the D.C. voltage across the capacitor 47 represents the mean pressure sensed by the transducer 20 or 20' (FIGS. 1, 2A-2F and 2H-2J) or the noninvasive transducer (in system of FIG. 2G) over a relatively long period, for example during the preceding fifteen (15) minutes or even longer for example a number of hours) or shorter (for example one hundred twenty (120) seconds being suitable in some cases. The D.C. voltage (first signal) which appears across the capacitor 47 thus represents a long term mean baseline pressure. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to the inverting and noninverting terminals of an operational amplifier 87, a difference D.C. voltage signal appearing as the output from the operational amplifier 87. As illustrated, the input terminals of the operational amplifier 87 are connected as they would be were pressure other than arterial pressure were involved. Were MAP to be the selected hemodynamic parameter, the terminals would be reversed. The D.C. output signal from the operational amplifier 87 is fed to a first input terminal of a comparator 88. The second input terminal of the comparator 88 is connected to the wiper of a potentiometer 89 which is connected between ground and a point of fixed D.C. potential, illustrated as being +15 volts, from an internal power supply bus.

Whenever the voltage supplied to the comparator 88 from the operational amplifier 87 exceeds the voltage supplied via the wiper from the potentiometer 89, a low (ZERO) level on the output terminal from the comparator 88 goes high (ONE), the ONE signal being coupled to a first input terminal of an AND circuit 90 which has its other input terminal coupled to the output terminal of a rate sensing circuit 83, which produces a ONE signal on its output terminal whenever the heart rate exceeds a predetermined value, for example 155 beats per minute. When the AND gate 90 receives ONE signals on both its input terminals, its output goes high (ONE) which enables a gate 56. The ONE signal from the AND gate 90 is also fed as an enabling input to a sample-and-hold circuit 57. The voltage representing current mean pressure appearing across the capacitor 51 is fed to the noninverting input terminal of an operational amplifier 60. The voltage representing mean baseline pressure appearing across the capacitor 47 is fed to the sample-and-hold circuit 57. Were MAP to be the selected hemodynamic parameter, the input terminals of the operational amplifier 60 would be reversed.

A D.C. output from the sample-and-hold circuit 57 is stored in a storage circuit, for the purpose of illustration shown as a capacitor 58. This stored voltage is supplied to the inverting input terminal of the operational amplifier 60 which has its noninverting input terminal connected to the output terminal of the gate 56, which when enabled, passes the D.C. voltage signal appearing across the capacitor 51 and representing current mean pressure to the operational amplifier 60. The output from the operational amplifier 60 is supplied to an input terminal of a comparator 61, which has its other input connected to the wiper of a potentiometer 62 connected between ground and the 3015 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. It is to be appreciated that the wipers of the potentiometers 89 and 62 can be adjusted independently. Thus, one can set the wiper of the potentiometer 62 so that the hemodynamic compromise must get worse than it was when the sample-and-hold circuit 57 is enabled before the output from the comparator 61 enables the D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse for effecting cardioversion is a truncated exponential pulse of about 25 Joules delivered approximately 17 seconds from onset of the hemodynamic compromise.

Once the capacitor 65 is charged to a sufficiently high D.C. voltage level, as determined by a comparator 67, which receives on one input terminal a voltage proportional to the D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A–2F and 2H–2J) or the rate sensing electrodes 212, 213 (FIG. 2G) and produces a pulse train in synchronism with the R-wave supplied from the electrodes 18a, 18b or the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A–2F and 2H–2J) or the electrodes 202 and 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse which is supplied, via the OR circuit 73, to the gate electrode of the SCR 74 causing the SCR to fire. The energy storage capacitor 65, which by then has been charged to a higher level, discharges, via the SCR 74 and the electrodes 13 and 14 (FIGS. 1, 2A–2F and 2H–2J) or the electrodes 202 and 204 (FIG. 2G), into the malfunctioning heart in an effort to effect defibrillation. The delay circuit 75 may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean pressure and current mean pressure returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure (which would cause the output of the comparator 61 to become ZERO, removing the enable signal from the converter 63), the capacitor 65 is recharged and discharged a number of additional times, for example three more times, in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to zero whenever either it reaches its maximum count of four or it fails to reach a count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 8, cardioverting/defibrillating D.C. pulses are delivered to the malfunctioning heart only when the rate and the pressure criteria are simultaneously satisfied. This can be viewed as a parallel rate-pressure algorithm.

In the event the rate criterion is met, but the pressure criteria are not; that is to say no hemodynamic compromise presents, the circuit of FIG. 8 nevertheless acts to enable an antitachycardia pacemaker 86 which supplies pacing signals to the pair of pacing electrodes 21, 22 (FIGS. 1, 2A-2F and 2H-2J) or the pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs are ONE, the antitachycardia pacemaker 86 is energized.

Figure 9A:
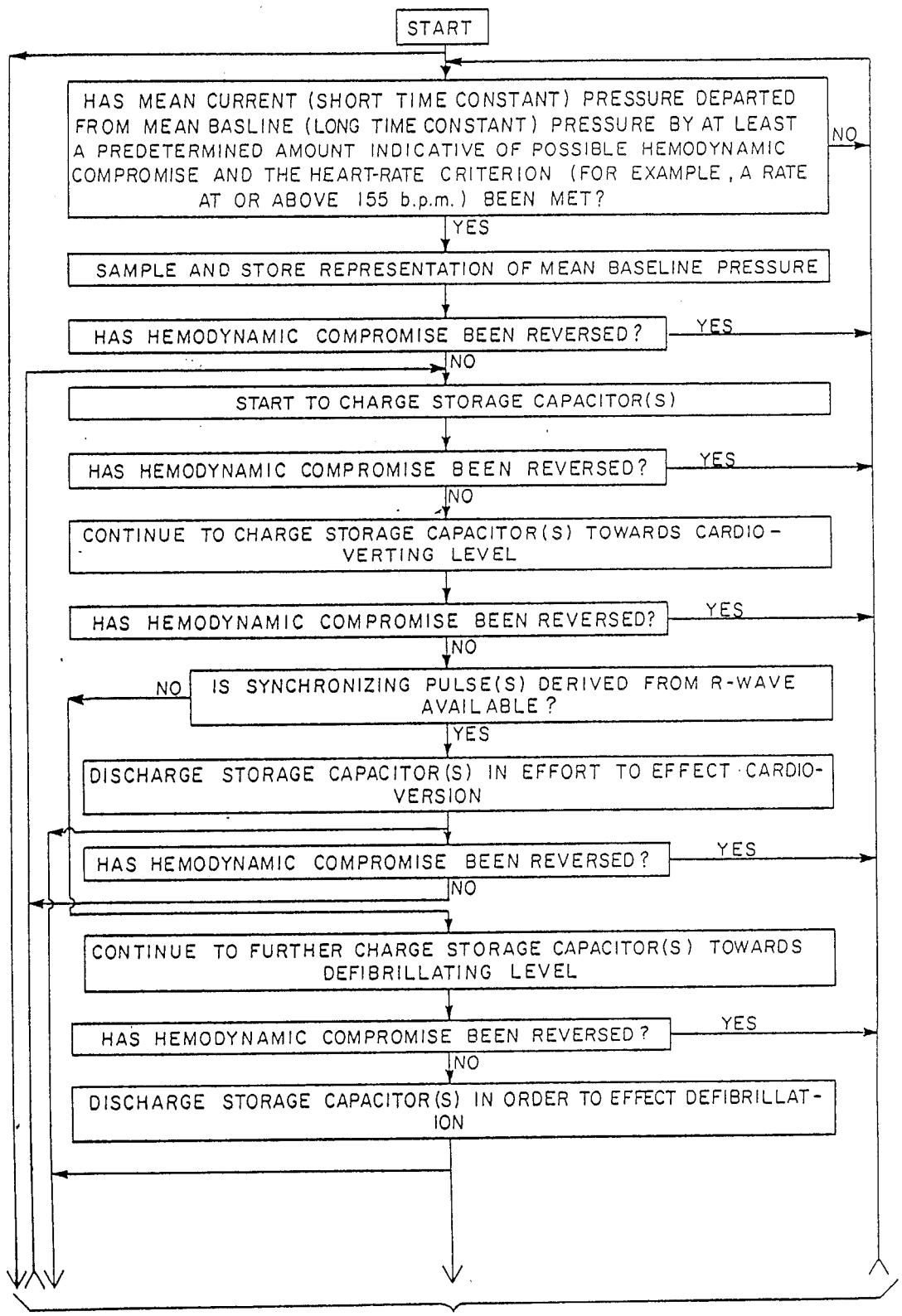
FIGS. 9A and 9B constitute a third exemplary flowchart of a series of actions or steps which may be carried out by the system illustrated in FIG. 8 and effect achievement of a corresponding method.
Figure 9B:
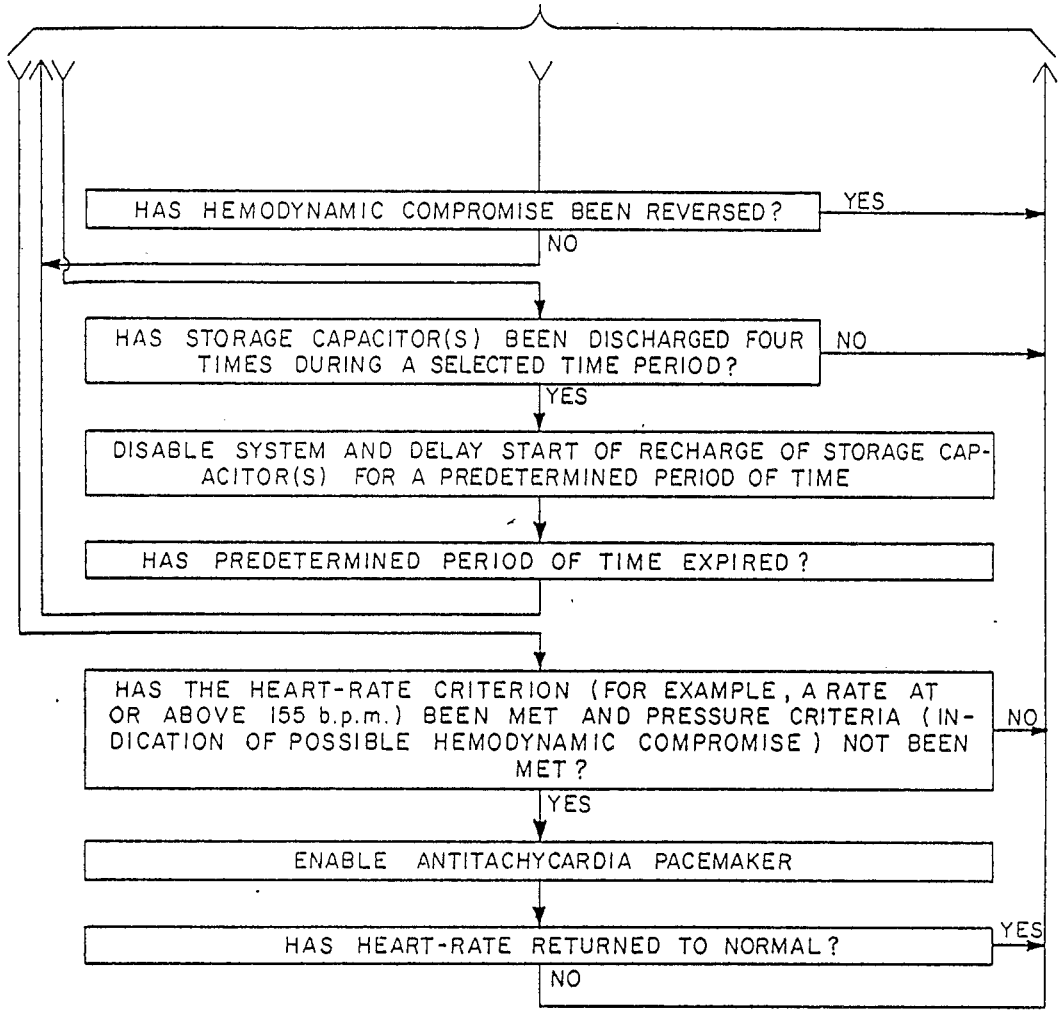

It is to be appreciated that the circuit described above may be considered, at least in part, to be a controller processor, which could be realized as a microprocessor, the processor being identified by the numeral 82. The processor 82, with its associated components, in effect carries out the steps set out in the flowchart of FIGS. 9A and 9B.

The circuit of FIG. 8 could be associated with a failsafe antibradycardia pacemaker, if desired.

Figure 15:
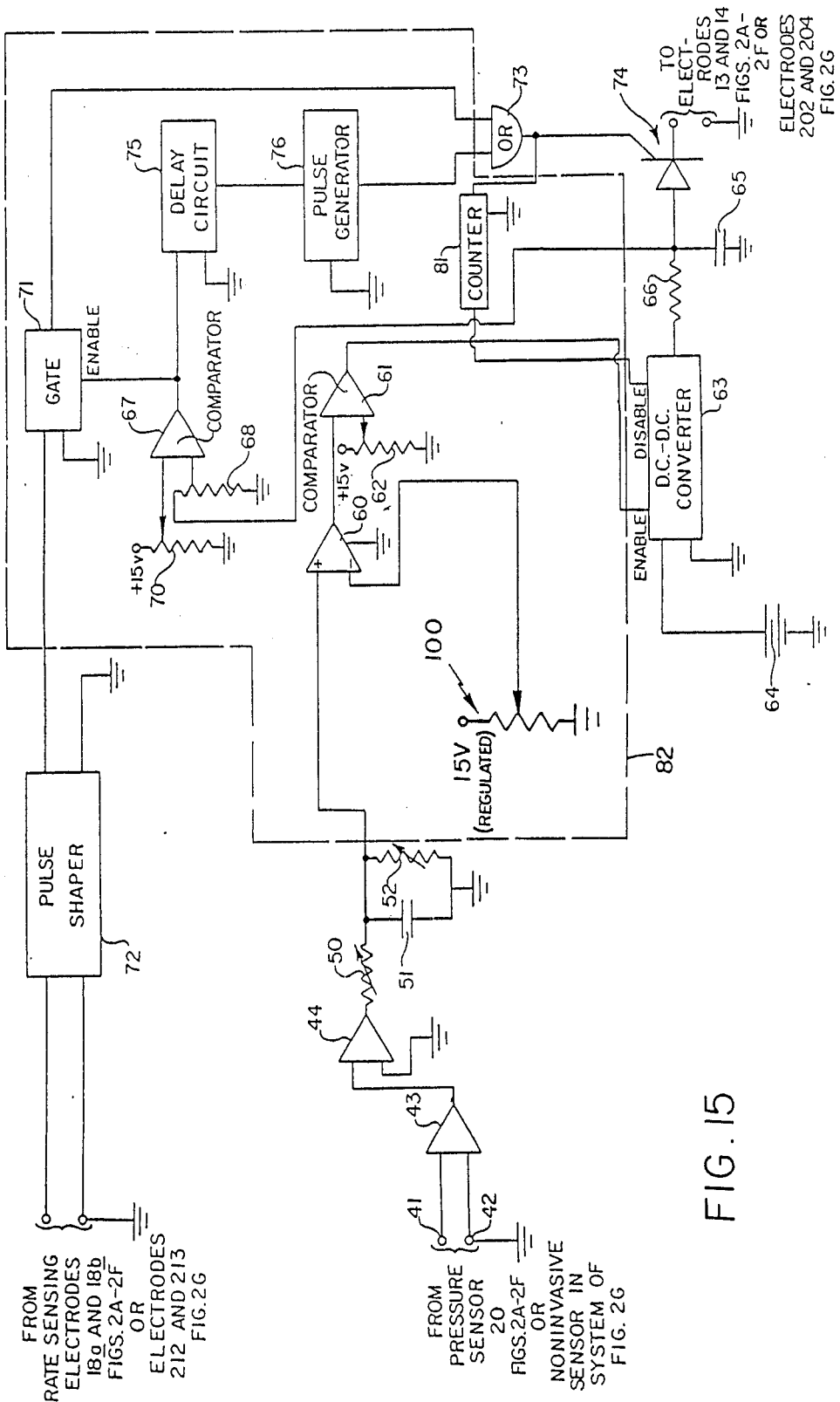
FIG. 15 is a partially block, schematic diagram of a hemodynamically responsive system for treating a malfunctioning heart in accordance with an exemplary embodiment of the invention which is pressure responsive.

Turning to FIG. 15, an exemplary embodiment of circuit components of the present invention, which may be positioned within the housing 12 (FIGS. 1 and 3) or the bed-side apparatus 208 (FIG. 2G), includes a pair of input terminals 41, 42 which receive the variable D.C. voltage output signal representing pressure from the pressure responsive transducer 20 or 20' (FIGS. 1, 2A-2F and 2H-2J) or noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to a buffer amplifier 44. The circuit of FIG. 15 is suitable for practicing the present invention using a pressure-only criteria.

A D.C. voltage level (first signal) representative of fixed baseline pressure appears on the wiper of a potentiometer 100 which may be set by a medical professional to suit the particular patient involved. The potentiometer 100 is connected, as illustrated, between system ground and a point of +15 volts, regulated. The medical professional, based on a patient's condition and history, could set the wiper of the potentiometer at a suitable patient-specific point, reflecting an appropriate baseline. It is to be understood that the point may be selected prior to implantation. The circuit may be adapted to enable the patient-specific set point to be changed, the set using radio and/or magnetic coupling (not shown).

The term "mean" as used herein is broad and includes the average value as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 or 20' (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds). The resistors 50 and 52 may be set by a medical professional to suit the particular patient involved, so far as what the most suitable period length (period of given length) for current data acquisition appears to be most suitable. Were the device already implanted, conventional radio or magnetic links could be used to change the setting of the variable resistors 50 and 51 were a patient's condition to make such adjustments desirable.

As illustrated the baseline and short term (current) D.C. voltage signals which appear respectively on the wiper of the potentiometer 100 and across the capacitor 51 are fed respectively to the inverting and noninverting terminals of an operational amplifier 60, a difference D.C. voltage signal appearing as the output from the operational amplifier 60. As shown, the inverting and noninverting terminals of the operational amplifier 60 are connected as they would be were pressures other than arterial pressures to be involved. Were MAP to be the hemodynamic parameter involved, the terminals would be reversed. The D.C. output signal from the operational amplifier 60 is fed to a first input terminal of a first comparator 61, the second input terminal of the comparator 61 is connected to the wiper of a potentiometer 62 which is connected between ground and a point of fixed D.C. potential, illustrated as being +15 volts, from an internal power supply bus.

Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or a capacitor pack), via a resistor 66 towards the high voltage. The capacitor 65 is of such size that it will store energy levels sufficient to produce the desired cardioverting/defibrillation pulses. The desired pulse may be a truncated exponential pulse of about 25 Joules delivered approximately 17 seconds from onset of the hemodynamic compromise. The pulse could, especially when defibrillation is being undertaken after a failed attempt to cardiovert, be delivered somewhat later and with a higher energy level.

Once the capacitor 65 is charged to a sufficiently high D.C. voltage level to provide sufficient energy to effect cardioversion, as determined by a comparator 67, which receives on one input terminal a voltage proportional to the increasing D.C. voltage across the capacitor 65, a highly resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input terminal connected to receive an output from a pulse shaper 72, which receives an input from the rate sensing electrodes 18a, 18b (FIGS. 1, 2A–2F and 2H–2J) or from the rate sensing electrodes 212, 213 (FIG. 2G) and produces a pulse train in synchronism with the R-wave supplied from the electrodes 18a, 18b or electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy then stored on the capacitor 65 (or the bank of capacitors) into the malfunctioning heart, via the electrodes 13 and 14 (FIGS. 1, 2A–2F and 2H–2J) or the electrodes 202 and 204 (FIG. 2G) in an effort to effect cardioversion, the discharge being in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more and enables a pulse generator 76 causing it to produce an output pulse to initiate defibrillation which is supplied, via the OR circuit 73, to the gate electrode of the SCR 74 causing the SCR to fire. The energy storage capacitor 65 (or the bank of capacitors), which by then has charged to a higher level discharges, via the SCR 74 and the electrodes 13 and 14 (FIGS. 1, 2A–2F and 2H–2J) or the electrodes 202 and 204 (FIG. 2G), into the malfunctioning heart in an effort to effect defibrillation, the energy level being higher than would have been the case had the capacitor been discharged three seconds earlier. The delay circuit may be composed of an RC circuit connected to the comparator 67 so that the capacitor thereof charges toward the ONE level slowly; for example the capacitor may take about three (3) seconds or more as indicated above to achieve the ONE level, allowing time to receive one or more synchronizing pulses from the pulse shaper 72, if present.

In the event the first pulse delivered to the heart fails to effect a correction in the pressure (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. An internal timer within the converter 63 holds the converter OFF for a given period so that the patient will not receive more shocks during this given period. At the end of the period the converter 63 returns to a READY condition and is again able to respond to an ENABLE signal from the comparator 61. The counter 81 resets itself to zero whenever it either reaches its maximum count of four or fails to reach the count of four within the given time period.

In the event cardioversion or defibrillation is successful, the short term mean current pressure (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the pressure condition sensed indicates that hemodynamic compromise is again present. In the event the short term mean current pressure returns to normal before the first cardioverting or defibrillating pulse is delivered, the output of the comparator goes to low (ZERO), removing the enable signal from the converter 63, thus stopping the charging of the capacitor 65.

Figure 16A:
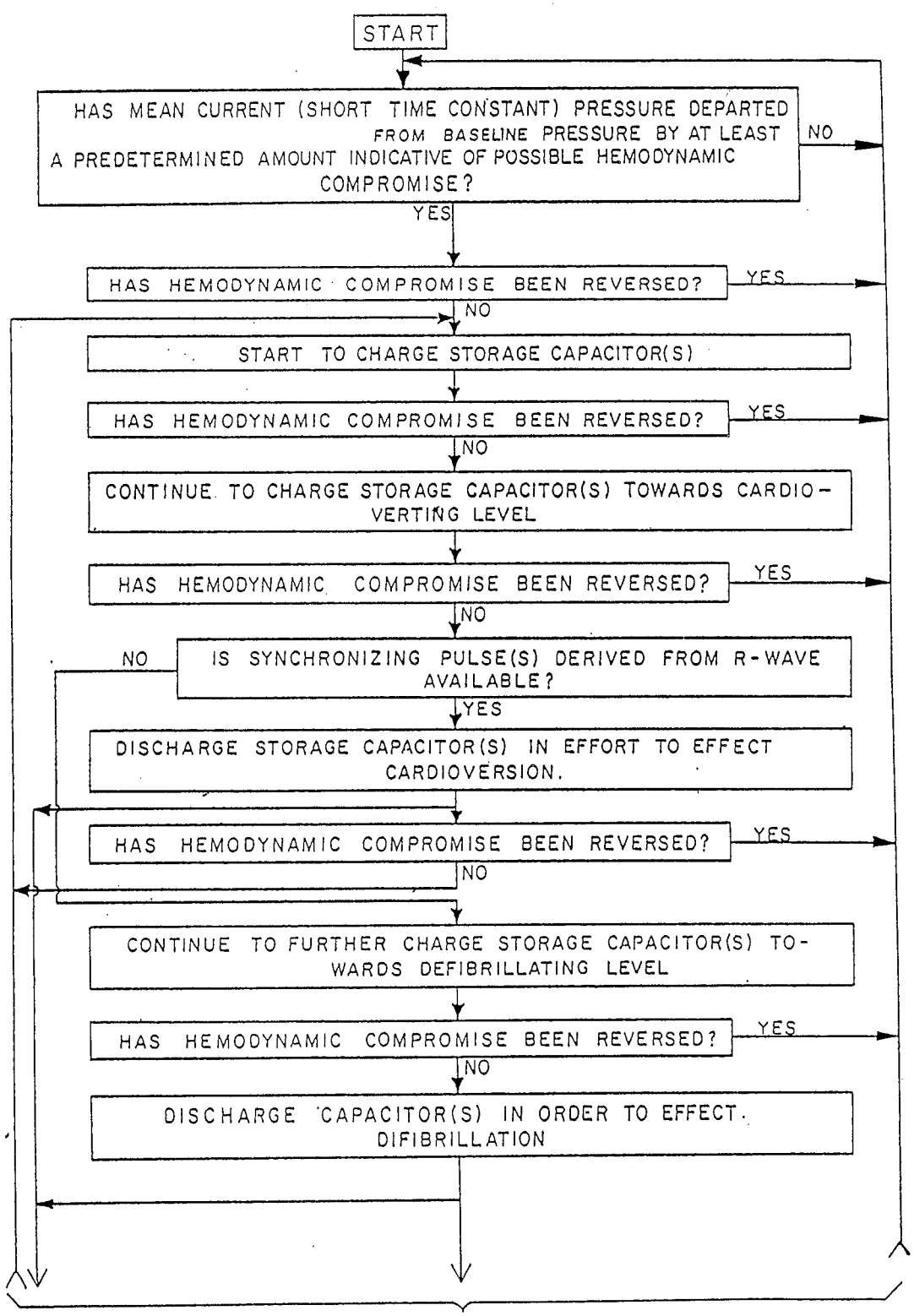
FIGS. 16A and 16B constitute an exemplary flowchart of a series of actions or steps which may be carried out by the system of the present invention illustrated in FIG. 15 and effect achievement of the invention in its method aspect.
Figure 16B:
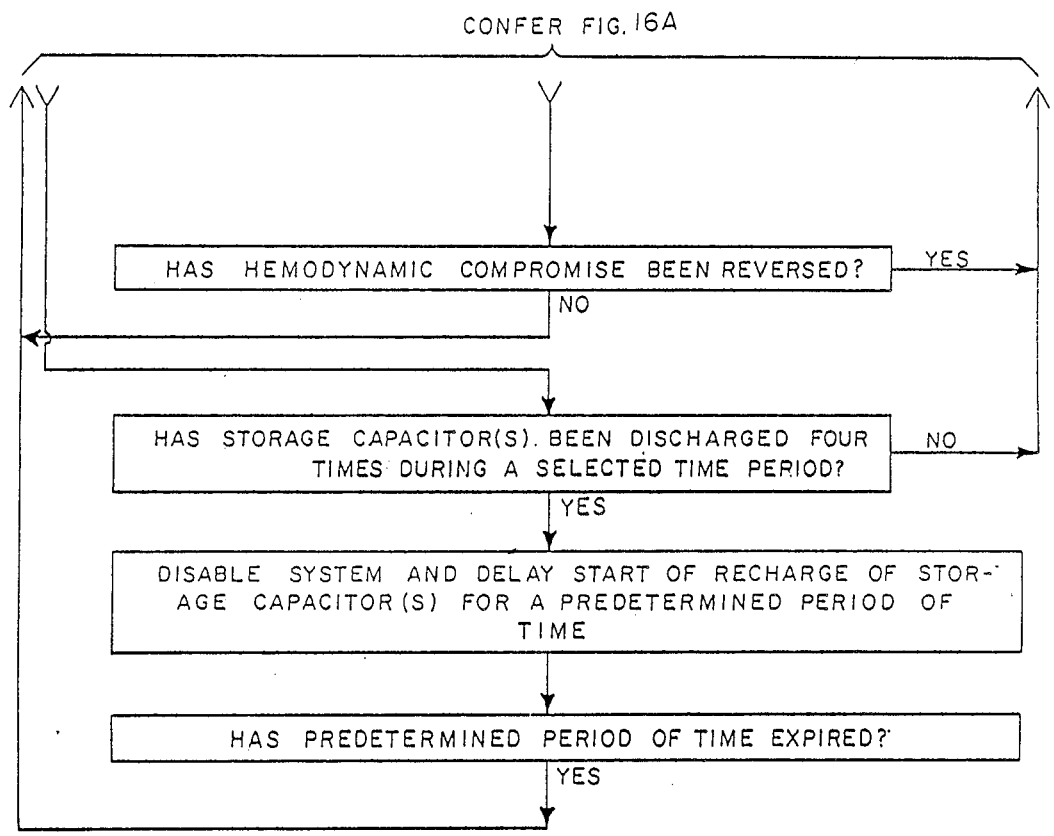

It is to be appreciated that the circuit of FIG. 15 described above may be considered, at least in part, to be a controller or processor, which could be realized as a microprocessor, the processor being identified by the numeral 82. The processor 82, with its associated components, in effect carries out the steps set out in the flowchart of FIGS. 16A and 16B.

The circuit of FIG. 15 could be associated with an antitachycardia pacemaker and/or an antibradycardia pacemaker, if desired.

Figure 17:
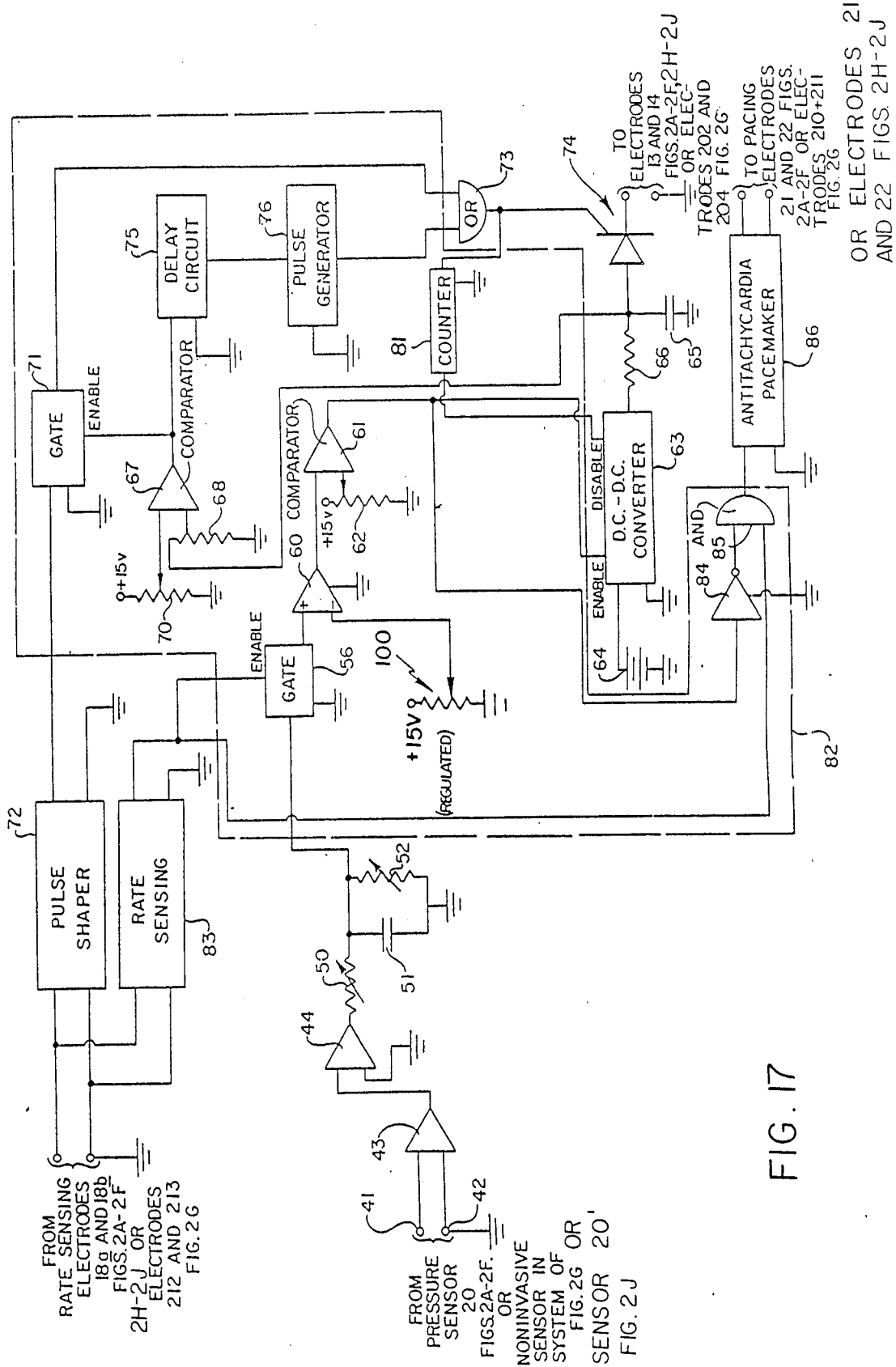
FIG. 17 is a partially block, schematic diagram of a hemodynamically responsive system for treating a malfunctioning heart in accordance with a further exemplary embodiment of the invention which is pressure and rate responsive.

Turning to FIG. 17, a second exemplary embodiment of the circuit components of the present invention, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 or 20' (FIGS. 1, 2A–2F and 2H–2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to a buffer amplifier 44. The circuit of FIG. 17, with associated components, is suitable for practicing the present invention in which both pressure and beating rate criteria are to be taken into account. The rate criterion is examined first and, if met, the pressure criteria are then considered.

A D.C. voltage level (first signal) provided on the wiper of a potentiometer 100, which is connected between ground and a regulated +15 volts source, represents a fixed baseline pressure. The wiper may be set by a medical professional taking into account the history and condition of the particular patient. The potentiometer 100 may be adjusted, possibly using conventional magnetic or radio links as noted above.

The term "mean" as used herein is broad and includes the average value, as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 or 20' (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds). As in the circuit of FIG. 15, the resistors 50 and 51 may be adjusted, taking into account the patient's possibly changing condition, possibly using conventional radio or magnetic links.

As illustrated the baseline and short term (current) D.C. voltage signals appear respective on the wiper of the potentiometer 100 and across the capacitor 51. The voltage (second signal) from the capacitor 51 is fed to the signal input terminal of a gate 56. A rate sensing circuit 83 is arranged to receive a beating rate (R-wave) signal from the rate sensing electrodes 18a, 18b (FIGS. 1, 2A-2F and 2H-2J) or from the rate sensing electrodes 212, 213 (FIG. 2G). Whenever the rate exceeds a given rate, for example 155 beats per minute, indicating tachycardia, the output terminal of the rate sensing circuit 83 goes from low (ZERO) to high (ONE). The ONE signal (first control signal) is supplied as an enabling input to the gate 56. The D.C. voltage representing current mean pressure appearing across the capacitor 51 is fed via the enabled gate 56 to the noninverting input terminal of an operational amplifier 60. The D.C. voltage (first signal) representing baseline pressure appearing on the wiper of the potentiometer 10 is supplied to the inverting input terminal of the operational amplifier 60 which has its noninverting input terminal connected to the output terminal of the gate 56 which, when enabled as noted above, passes the D.C. voltage signal appearing across the capacitor 51 and representing current mean pressure to the operational amplifier 60. As illustrated, the input terminals of the operational amplifier 60 are connected as they would be to receive signals other than arterial pressure. Were MAP to be the selected hemodynamic parameter, the terminals would be reversed.

The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) and the signal (second control signal) is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or a pack of capacitors), via a resistor 66 towards the high voltage. The capacitor 65 is of such size that it will store energy levels sufficient to produce the desired cardioverting/defibrillation pulses. The desired pulse for cardioversion may be a truncated exponential pulse of about 25 Joules delivered approximately 17 seconds from onset of the hemodynamic compromise.

Once the capacitor 65 is charged to a sufficiently high D.C. voltage level to provide sufficient energy to effect cardioversion, as determined by a comparator 67, which receives on one input terminal a voltage proportional to the instant D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or from the rate sensing electrodes 212, 213 (FIG. 2G) and produces a pulse train in synchronism with the R-wave supplied from the electrodes 18a, 18b or from the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A-2F and 2H-2J) or the electrodes 202, 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse to initiate defibrillation. The pulse is supplied, via the OR circuit 73, to the gate electrode of the SCR 74 causing the SCR to fire. The energy storage capacitor 65 (or a pack of capacitors), which during the elapsed three seconds has charged to a higher level, discharges, via the SCR 74 and the electrodes 13 and 14 (FIGS. 1, 2A-2F and 2H-2J) or electrodes 202 and 204 (FIG. 2G), into the malfunctioning heart via the electrodes 13 and 14 (FIGS. 1, 2A-2F and 2H-2J) or electrodes 202 and 204 (FIG. 2G) in an effort to effect defibrillation, the energy level being higher than it would had been had discharge been effected three (3) or more seconds earlier. The delay circuit may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

In the event the first pulse delivered to the heart fails to effect a correction in the pressure by overcoming the hemodynamic compromise (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to ZERO count whenever it either reaches its maximum count of four or fails to reach the count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 17, cardioverting/defibrillating D.C. pulses are delivered to the malfunctioning heart only when the rate criterion is first satisfied and, thereafter, the pressure criteria also satisfied. This can be viewed as a series rate-pressure algorithm.

In the event the rate criterion is met, but the pressure criteria are not; that is to say no hemodynamic compromise presents, the circuit of FIG. 17 nevertheless acts to enable an antitachycardia pacemaker 86 which supplies pacing signals to the pair of pacing electrodes 21, 22 (FIGS. 1, 2A–2F and 2H–2J) or the pair of pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs to the AND circuit 85 are ONE, the antitachycardia pacemaker 86, which may be any one of a number of conventional types is energized.

In the event cardioversion or defibrillation is successful, the short term mean current pressure (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the pressure condition sensed indicates that hemodynamic compromise is again present. In the event the short term current pressure returns to normal before any cardioverting or defibrillating pulses are delivered (as in the case of FIG. 15), the enable signal is revived from the converter 63 and the charging of the capacitor 65 stops.

Figure 18A:
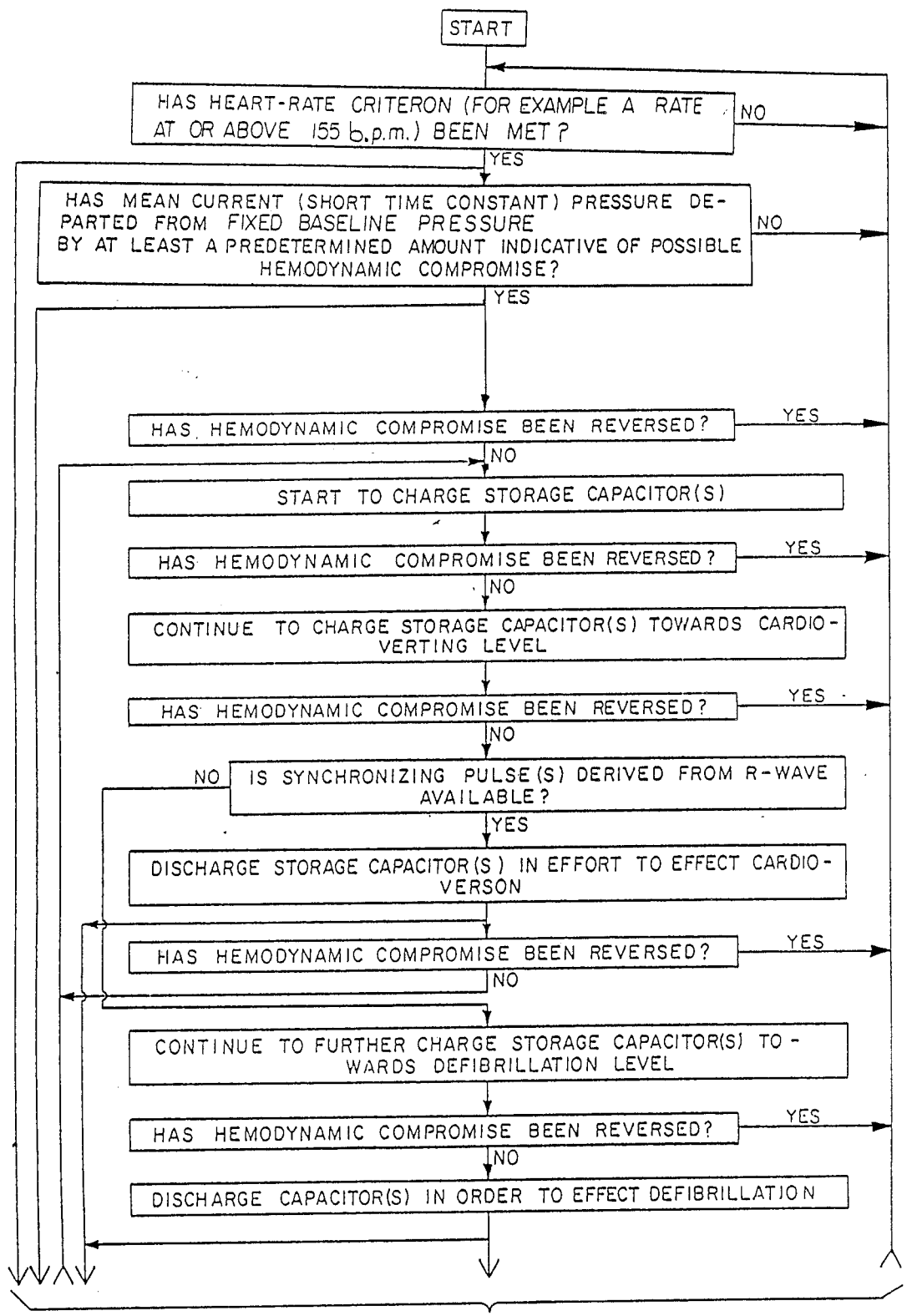
FIGS. 18A and 18B constitute a further exemplary flowchart of a series of actions or steps which may be carried out by the system of the present invention illustrated in FIG. 17 and effect achievement of the invention in its method aspect.
Figure 18:
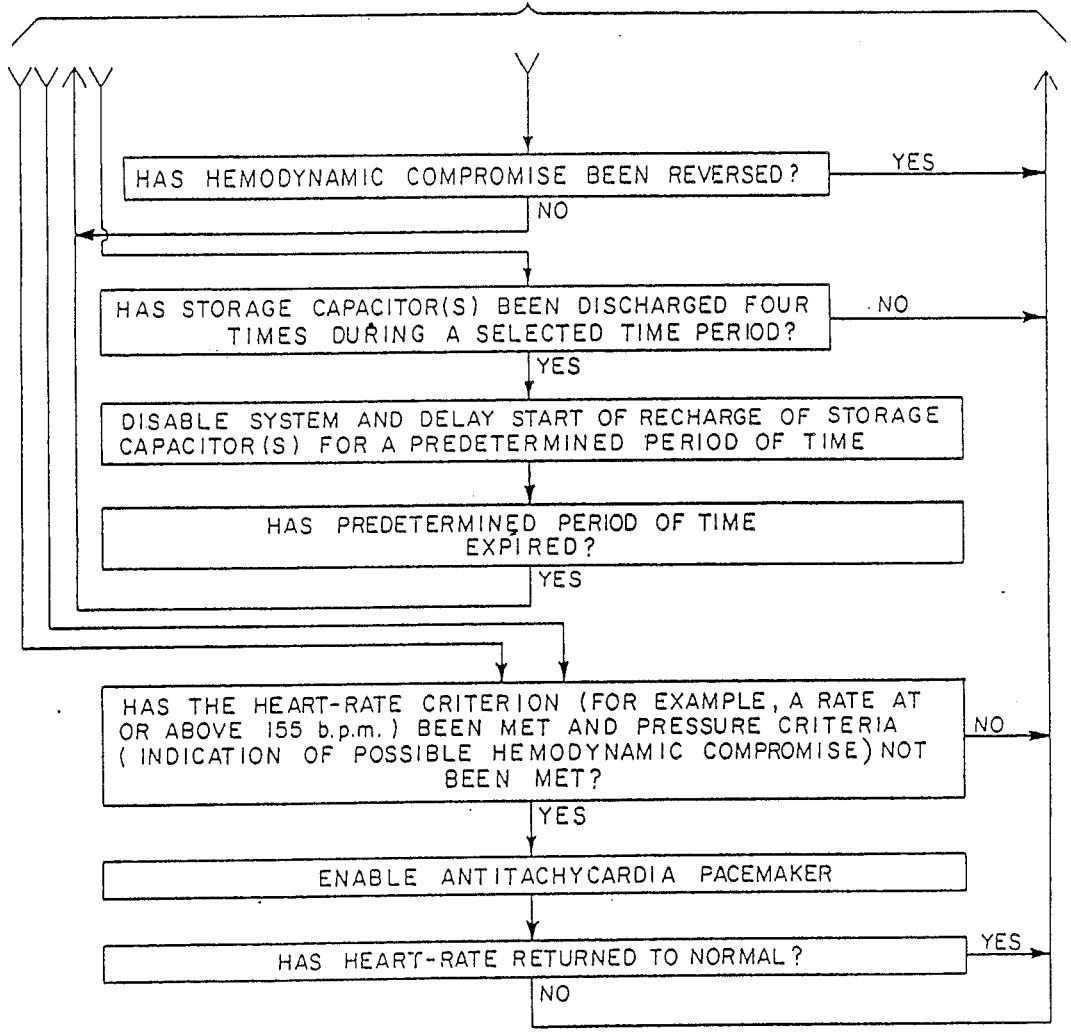

It is to be appreciated that the circuit of FIG. 17 described above may be considered, at least in part, to be a processor, which could be realized as a microprocessor, the processor being identified by the numeral 82. The processor 82, with its associated components, in effect carries out the steps set out in the flowchart of FIGS. 18A and 18B.

It is to be understood that the system of FIG. 17 could be associated with a failsafe antibradycardia pacing system, if desired.

Figure 19:
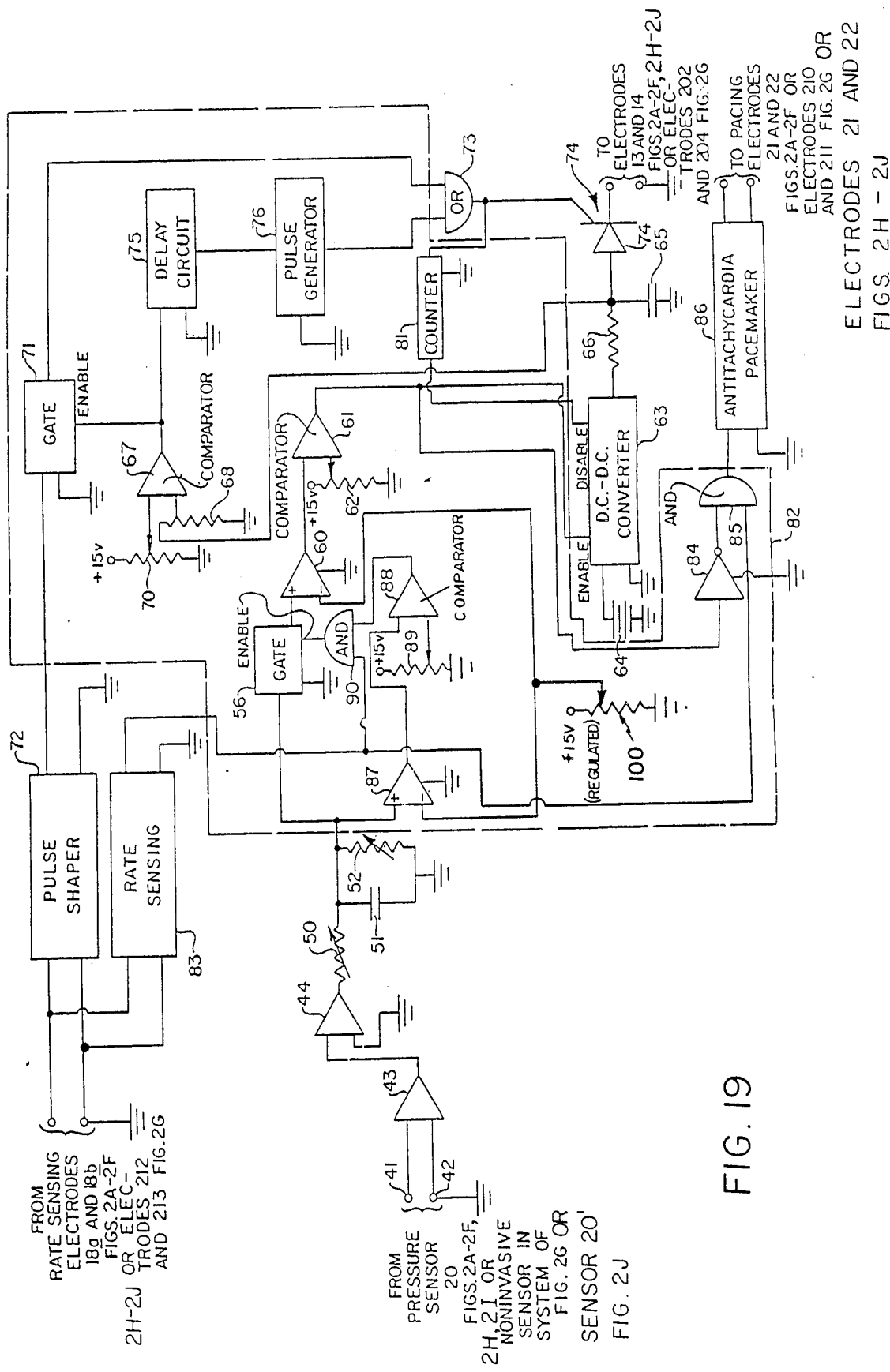
FIG. 19 is a partially block, schematic diagram of a hemodynamically responsive system for treating a malfunctioning heart which is a variant of the circuit of FIG. 17.

Turning to FIG. 19, a third exemplary embodiment of the circuit components of the present invention, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 or 20' (FIGS. 1, 2A–2F and 2H–2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to buffer amplifier 44. The circuit of FIG. 19 can be used in practicing the present invention using both rate and pressure criteria. In this case the rate and pressure criteria must exist simultaneously to enable the system.

A D.C. voltage level (first signal) appears on the wiper of a potentiometer 100, which is connected between ground and a regulated +15 volt source, the signal representing fixed baseline pressure. The wiper (as in the circuits of FIGS. 15 and 17) may be set by a medical professional in accordance with needs of a specific patient and may be adjusted later, if desired, using radio or magnetic techniques.

The term "mean" as used herein is broad and includes the average value, as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage which appears across the capacitor 51 represents the 5 short term mean pressure sensed by the transducer 20 or 20' (FIGS. 1, 2A–2F and 2H–2J) or the noninvasive transducer (in system of FIG. 2G) over a relatively short period, for example, during the preceding fifteen (15) seconds or longer (for example 60 seconds) or shorter (for example six seconds). The size of the resistors 50 and 51 (as in the circuits of FIGS. 15 and 17) may be adjusted, a desirable feature were a patient's condition or needs to change.

As illustrated the baseline and short term (current) D.C. voltage signals which respectively appear on the wiper 100 of the potentiometer 100 and across the capacitor 51 are fed respectively to the inverting and noninverting terminals of an operational amplifier 87, a difference D.C. voltage signal appearing as the output from the operational amplifier 87. As illustrated, the input terminals of the operational amplifier 87 are connected as they would be were pressure other than arterial pressure were involved. Were MAP to be the selected hemodynamic parameter, the terminals would be reversed. The D.C. output signal from the operational amplifier 87 is fed to a first input terminal of a comparator 88. The second input terminal of the comparator 88 is connected to the wiper of a potentiometer 89 which is connected between ground and a point of fixed D.C. potential, illustrated as being +15 volts, from an internal power supply bus.

Whenever the voltage supplied to the comparator 88 from the operational amplifier 87 exceeds the voltage supplied via the wiper from the potentiometer 89, a low (ZERO) level on the output terminal from the comparator 88 goes high (ONE), the ONE signal being coupled to a first input terminal of an AND circuit 90 which has its other input terminal coupled to the output terminal of a rate sensing circuit 83, which produces a ONE signal on its output terminal whenever the heart rate exceeds a predetermined value, for example 155 beats per minute. When the AND gate 90 receives ONE signals on both its input terminals, its output goes high (ONE) which enables a gate 56. The voltage (second signal) representing current mean pressure appearing across the capacitor 51 is fed to the noninverting input terminal of an operational amplifier 60. The voltage (first signal) representing fixed baseline pressure appearing on the wiper of the potentiometer 100 is fed to the inverting input terminal of the operational amplifier 60. Were MAP to be the selected hemodynamic parameter, the input terminals of the operational amplifier 60 would be reversed. A D.C. output from the sample-and-hold circuit 57 is stored in a storage. The operational amplifier 60 which has its noninverting input terminal connected to the output terminal of the gate 56, which when enabled, passes the D.C. voltage signal appearing across the capacitor 51 and representing current mean pressure to the operational amplifier 60. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. It is to be appreciated that the wipers of the potentiometers 89 and 62 can be adjusted independently. Thus, one can set the wiper of the potentiometer 62 so that the hemodynamic compromise must get worse than it was when the gate 56 was opened before the output from the comparator 61 enables the D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or capacitor pack), via a resistor 66 towards the high voltage. The capacitor 65 is of such size that it will store energy levels sufficient to produce the desired cardioverting/defibrillation pulses. The desired pulse for effecting cardioversion may be a truncated exponential pulse of about 25 Joules delivered approximately 17 seconds from onset of the hemodynamic compromise.

Once the capacitor 65 is charged to a sufficiently high D.C. voltage level, as determined by a comparator 67, which receives on one input terminal a voltage proportional to the D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or the rate sensing electrodes 212, 213 (FIG. 2G) and produces a pulse train in synchronism with the R-wave supplied from the electrodes 18a, 18b or the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A-2F and 2H-2J) or the electrodes 202 and 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse which is supplied, via the OR circuit 73, to the gate electrode of the SCR 74 causing the SCR to fire. The energy storage capacitor 65, which by then has been charged to a higher level, discharges, via the SCR 74 and the electrodes 13 and 14 (FIGS. 1, 2A-2F and 2H-2J) or the electrodes 202 and 204 (FIG. 2G), into the malfunctioning heart in an effort to effect defibrillation. The delay circuit 75 may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

In the event the first pulse delivered to the heart fails to effect a correction in the pressure (which would cause the output of the comparator 61 to become ZERO, removing the enable signal from the converter 63), the capacitor 65 is recharged and discharged a number of additional times, for example three more times, in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to zero whenever either it reaches its maximum count of four or it fails to reach a count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 19, cardioverting/defibrillating D.C. pulses are delivered to the malfunctioning heart only when the rate and the pressure criteria are simultaneously satisfied. This can be viewed as a parallel rate-pressure algorithm.

In the event the rate criterion is met, but the pressure criteria are not; that is, to say no hemodynamic compromise presents, the circuit of FIG. 19 nevertheless acts to enable an antitachycardia pacemaker 86 which supplies pacing signals to the pair of pacing electrodes 21, 22 (FIGS. 1, 2A-2F and 2H-2J) or the pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs are ONE, the antitachycardia pacemaker 86 is energized.

In the event cardioversion or defibrillation is successful, the short term mean current pressure (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the pressure condition sensed indicates that hemodynamic compromise is again present.

Figure 20A:
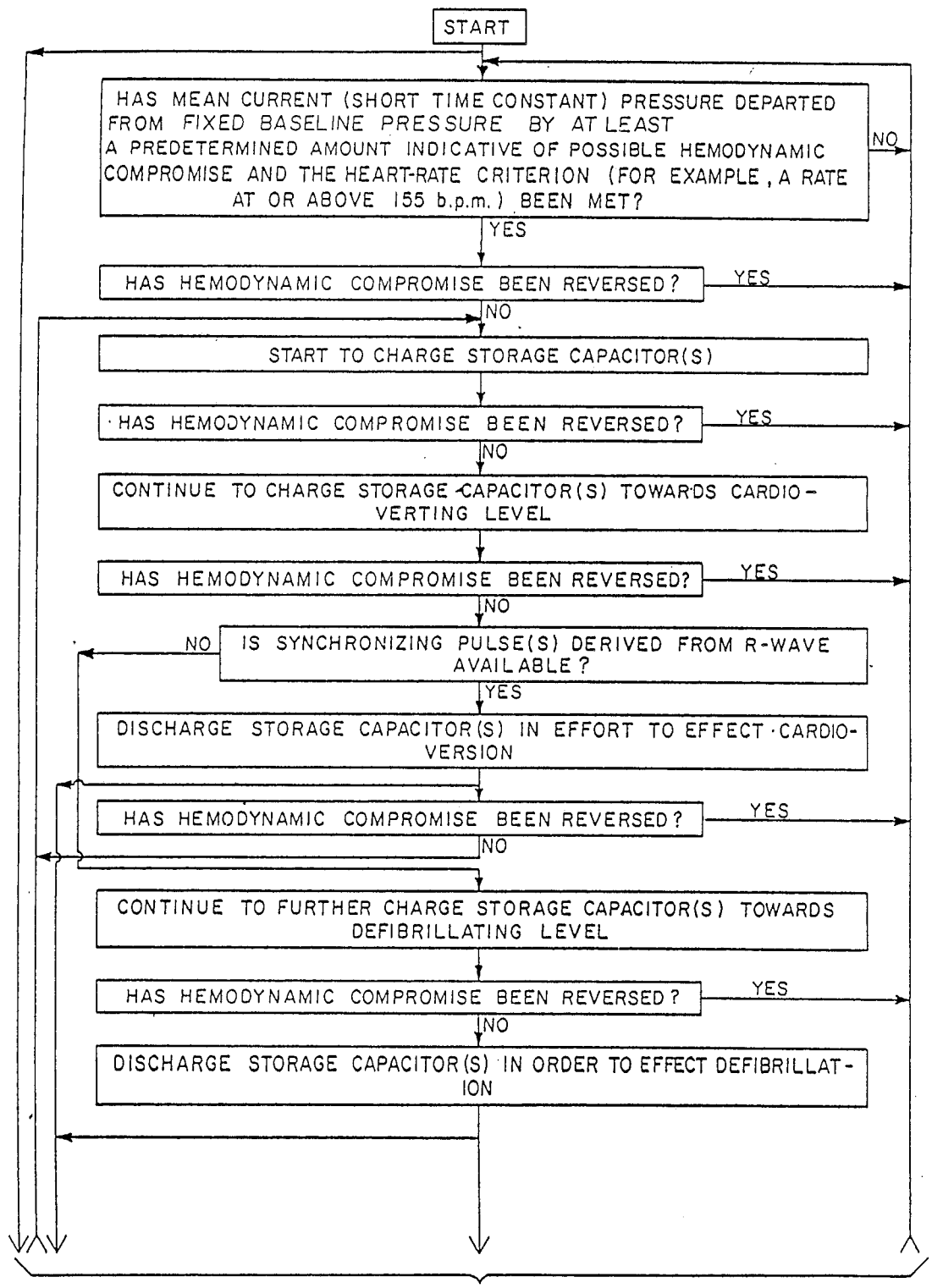
FIGS. 20A and 20B constitute an additional exemplary flowchart of a series of actions or steps which may be carried out by the system of the present invention as illustrated in FIG. 19 and effect achievement of the invention in its method aspect.
Figure 20B:
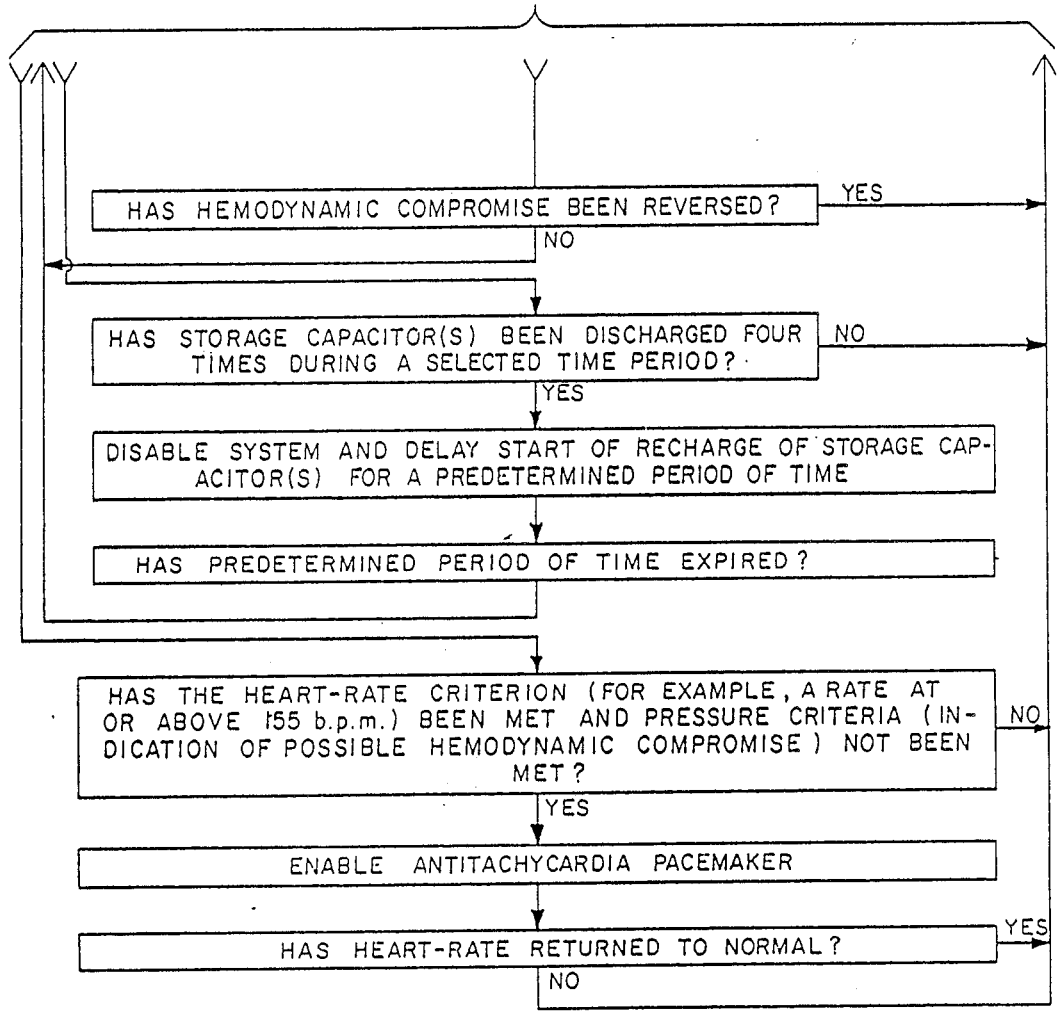

It is to be appreciated that the circuit of FIG. 19 described above may be considered, at least in part, to be a controller processor, which could be realized as a microprocessor, the processor being identified by the numeral 82. The processor 82, with its associated components, in effect carries out the steps set out in the flowchart of FIGS. 20A and 20B.

The circuit of FIG. 19 could be associated with a failsafe antibradycardia pacemaker, if desired.

Figure 10:
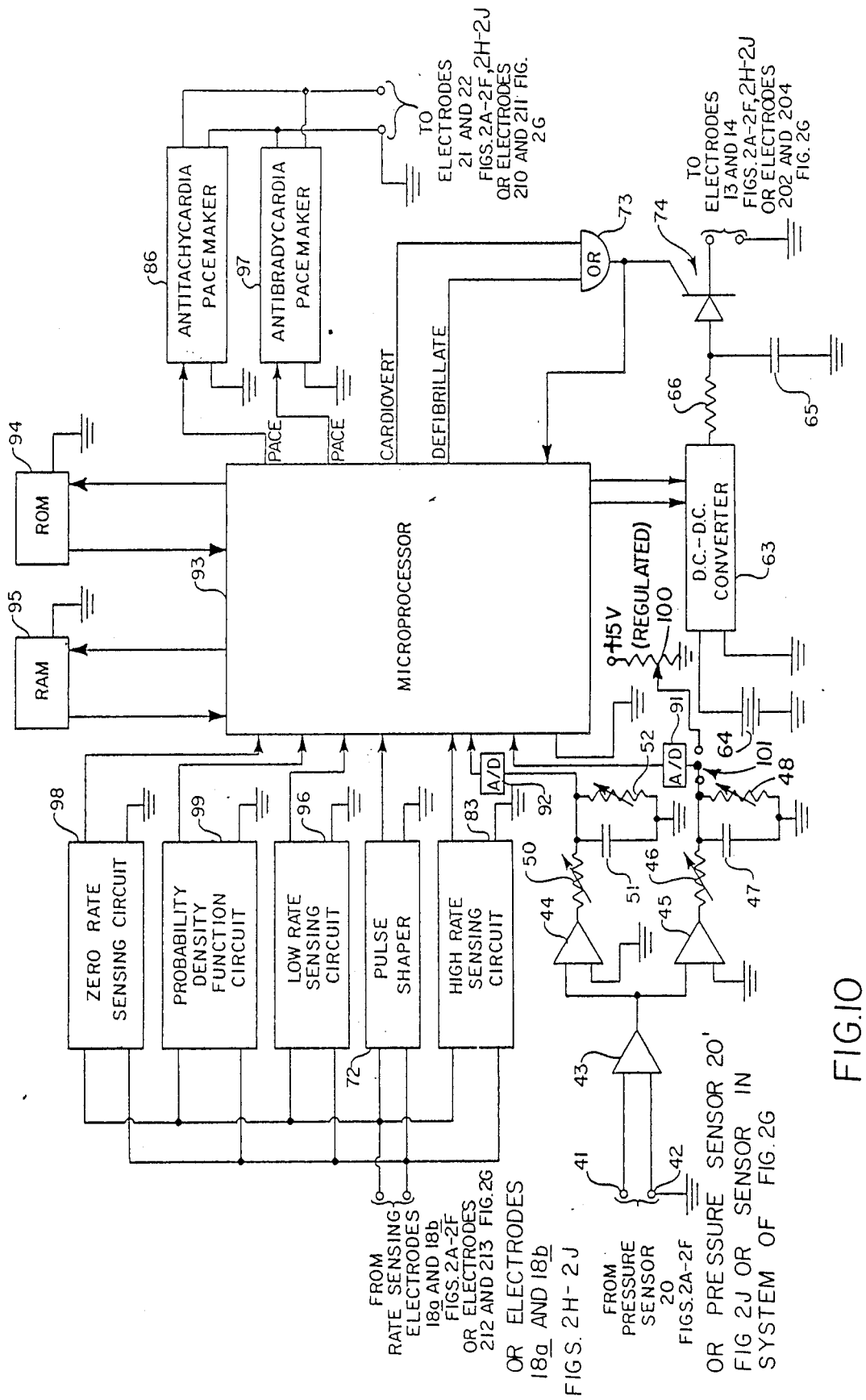
FIG. 10 is a partially block, schematic diagram of a hemodynamically responsive system for treating a malfunctioning heart which provides a microprocessor implementation in accordance with preferred embodiments of the present invention, as well as those illustrated in FIGS. 4, 6 and 8.

Turning to FIG. 10, a fourth exemplary embodiment of circuit components of a system for treating a malfunctioning heart, which may be positioned within the housing 12 (FIGS. 1 and 3) or in the apparatus 208 (FIG. 2G) or used in a portable system which may be carried on the body of a patient or used in fixed installation, such as in ICU's, CCU's, hospital rooms and the like includes a pair of input terminals 41, 42 which receive the variable D.C. voltage output signal representing pressure from the pressure responsive transducer 20 or 20' (FIGS. 1, 2A-2F and 2H-2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 10 can be used in practicing the present invention using either pressure criterion alone or both rate and pressure criteria (either in parallel or series). The circuit of FIG. 10 can be used to carry out the methods, illustrated as algorithms in the flowcharts of FIGS. 5A, 5B and 7A, 7B and 9A, 9B, 16A, 16B and 18A, 18B and 20A, 20B. The circuit of FIG. 10 can be considered as a digital, microprocessor-based version of the hand-wired analogue circuitry shown in FIGS. 4, 6 and 8, when the single-pole, double-throw switch 101 is set as shown. In the other position of the switch 101, the circuit can be considered to be a digital, microprocessor-based version of the hand-wired analogue circuitry illustrated in FIGS. 15, 17 and 19. Of course, the microprocessor-based circuit of FIG. 10 could be programmed to carry out other routines. For example, were a rate criterion to be satisfied, the circuit could be arranged (1) simply to monitor pressure, (2) to effect antitachycardia pacing and/or to cardiovert. As further examples, were both rate and pressure criteria to be satisfied, the circuit of FIG. 10 could be programmed (1) to effect antitachycardia pacing and/or (2) to cardiovert/defibrillate. Moreover, the selected interventions could be programmed so that when one is tried and fails, another is tried and so on. For example, if a tachycardia were detected regardless of whether or not hemodynamic compromise is present an antitachycardia pacemaker would attempt early to revert the arrhythms to normal and if this fails cardioversion/defibrillation would then attempt the same. A detailed discussion of one possible program is discussed below.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage (first signal) across the capacitor 47 represents the mean pressure sensed by the transducer 20 or 20' (FIGS. 1, 2A-2F and 2H-2J) or the noninvasive transducer (in system of FIG. 2G) over a relatively long period, for example during the preceding fifteen (15) minutes or even longer (for example a number of hours) of shorter (for example 120 seconds) being suitable in some cases. The D.C. voltage level across the capacitor 47 thus represents a long term mean baseline pressure. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the resistor 51 represents the short term mean pressure sensed by the transducer 20 or 20' (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively via respective analogue-to-digital converters (A/D's) 91 and 92 to respective inputs of a microprocessor 93. The A/D converters 91 and 92, in operation, convert the respective analogue signals which appear across capacitors 47 and 51 into corresponding digital signals for processing by the microprocessor 93, the microprocessor having associated therewith a ROM 94, which supplies programmed instructions to the microprocessor, and a RAM 95, which stores and supplies digital signal representations of pressure-related signals from and to the microprocessor.

Another input of the microprocessor 93 is supplied with high (ONE) and low (ZERO) signals from a high rate sensing circuit 83, which produces a ONE signal whenever the heart rate, as sensed by the electrodes 18a and 18b (FIGS. 2A-2F and 2H-2J) or by the electrodes 212 and 213 (FIG. 2G), exceeds a predetermined rate, for example a rate of 155 b.p.m. The actual rate selected would, of course, depend on the individual patient and a professional opinion as to his or her condition. A pulse shaper 72, which also receives an input from the rate sensing electrodes 18a and 18b (FIGS. 2A-2F and 2H-2J) or from the rate sensing electrodes 212 and 213 (FIG. 2G), is provided to supply narrow D.C. pulses to the microprocessor 93; if present, these pulses would be used as synchronizing pulses for cardioversion.

An antitachycardia pacemaker 86 is connected to an output terminal of the microprocessor 93 to receive therefrom a pace enable signal to, in effect, enable or turn on the pacemaker 86 under the command of the microprocessor 93. Two other output terminals from the microprocessor 93 provide respective cardiovert and defibrillate command signals to an OR circuit 73, which cooperates with a D.C.-to-D.C. converter 63, a battery 64, a charging resistor 66, storage capacitor 65 and a SCR 74 in the same manner as the corresponding circuit components having the same reference numerals function in the hand-wired circuits illustrated in FIGS. 4, 6 and 8. The output of the OR gate 73 is also supplied to an input terminal of the microprocessor 93, supplying signals to a counting means within the microprocessor 93 which corresponds to the counter 81 (FIGS. 4, 6 and 8).

As thus far described, the circuit of FIG. 10 can carry out the methods defined in the flowcharts of FIGS. 5A, 5B and 7A, 7B and 9A, 9B, the respective programs being supplied by the ROM 94. In operation, the circuit of FIG. 10, with the switch 101 set as illustrated, can be seen as a microprocessor realization of the hand-wired analogue circuits of FIGS. 4, 6 and 8. With the switch 101 set in its other position, the capacitor 47 and the resistor 48 are disconnected from the input to the A/D converter 91 and the wiper of the potentiometer 100 connected thereto. The voltage which appears on the wiper of the potentiometer 100 thus constitutes the first signal, representing in this case the fixed baseline pressure. The circuit of FIG. 10 when so connected on a carry out the methods defined in the flowcharts of FIGS. 16A, 16B and 18A, 18B and 20A, 20B. It is to be appreciated that the circuit of FIG. 10 can be programmed to effect somewhat different routines and be provided with additional inputs, as well.

If desired for example, a low rate sensing circuit 96 could be provided, its input being coupled to the rate sensing electrodes 18a and 18b (FIGS. 2A-2F and 2H-2J) or the sensing electrodes 212 and 213 (FIG. 2G). The low rate sensing circuit 96 supplies a high (ONE) signal to an input terminal whenever the beating rate, as sensed by the electrodes 18a and 18b or the electrodes 212 and 213, falls below a given rate, for example 45 b.p.m., indicative of bradycardia. Under these conditions (provided the rate were not zero), the microprocessor 93 would provide a command enable signal to an antibradycardia pacemaker 97. When enabled, the pacemaker 97 would supply bradycardia-correcting pacing signals to a patient's heart via the pacing electrodes 21 and 22 (FIGS. 1, 2A-2F and 2H-2J) or the pacing electrodes 210 and 211 (FIG. 2G).

If desired, a zero rate sensing circuit 98, responsive to output from the rate sensing electrodes 18a and 18b (FIGS. 2A-2F and 2H-2J) or the rate sensing electrodes 212 and 213 (FIG. 2G) can be provided. This zero rate sensing circuit 98 produces a high (ONE) output signal whenever the beating rate is zero, indicating the heart has stopped beating (sometimes referred to as going "flat line"). This may represent either asystole or fine ventricular fibrillation. Under this condition, the microprocessor 93 is programmed to first effect a charging and discharging of the storage capacitor 65, supplying a ONE signal via its command defibrillate output connection to the OR gate 73 and then to effect antibrachycardia pacemaking after a given number of capacitor(s) discharges (say 4) if no hemodynamic improvement is noted. The order of defibrillation and pacemaking may be programmed in a reverse manner as desired.

The circuit of FIG. 10 includes, if desired, a narrow window probability density function circuit 99, which has its input coupled to the sensing electrodes 18a and 18b or sensing electrodes 212 and 213. The probability density function circuit may be of the type disclosed in U.S. Pat. Nos. 4,184,493, 4,202,340 and 4,475,551 of Langer et al. and which produce a high (ONE) output signal whenever fine ventricular fibrillation is present. This ONE output is supplied to an input of the microprocessor 93 which, in accordance with its program stored in the ROM 94, effects the charging and discharging of the storage capacitor 65, supplying via its command defibrillate output a ONE signal to the OR gate 73 to initiate discharge.

Conventional antitachycardia systems function primarily as rate-only sensing devices and perform inadequately in differentiating hemodynamically stable from unstable tachycardias. Consequently, in the course of developing the present invention, mean right atrial (MRAP), mean right ventricular (MRVP), and mean arterial pressures (MAP) were studied by the applicant for determining if a basis was present to distinguish significant arrhythmias and serve as a basis for improving antitachycardia systems.

Hemodynamic responses to rapid atrial and ventricular pacing were examined in 10 closed-chest anesthetized dogs. Pressure monitoring catheters placed in the femoral artery, high right atrium (HRA), and right ventricular apex (RVA) measured MAP, MRAP, and MRVP at baseline heart rates and after 30 and 60 sec. rapid HRA and RVA pacing. Pressures recorded during rapid pacing (average of the pressures at 30 and 60 sec. of pacing) at pacing rates of 180, 250, and 280/min. were compared to those recorded initially at baseline heart rates.

Figure 11:
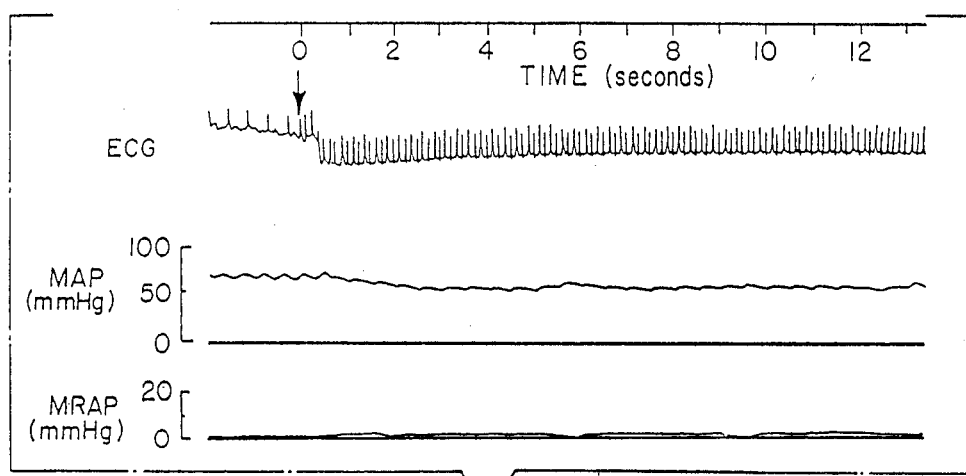
FIGS. 11–13 are respective graphical representations along a time axis of a rate wave (R-wave), mean arterial pressure (MAP) and mean right atrial pressure (MRAP) of a canine subject respectively under high right atrial pacing, right ventricle apex pacing and in ventricular fibrillation, useful in understanding the present invention.
Figure 12:
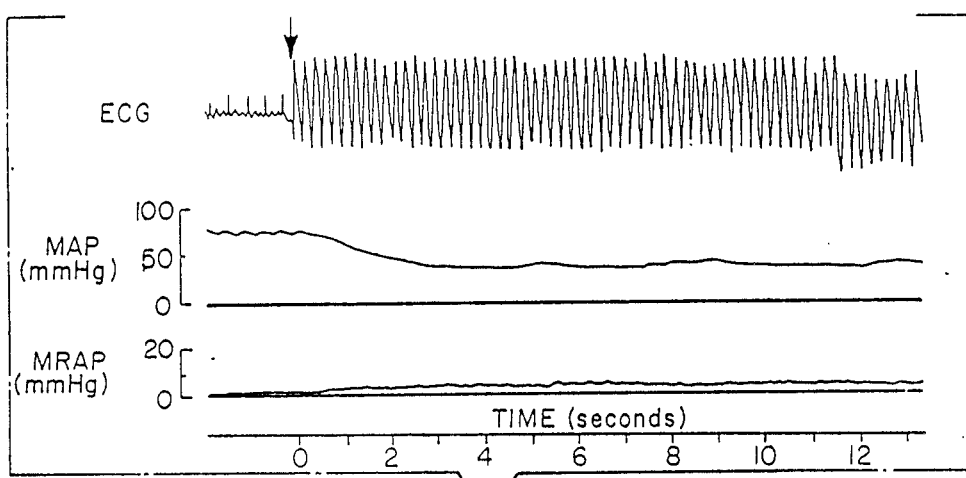
Figure 13:
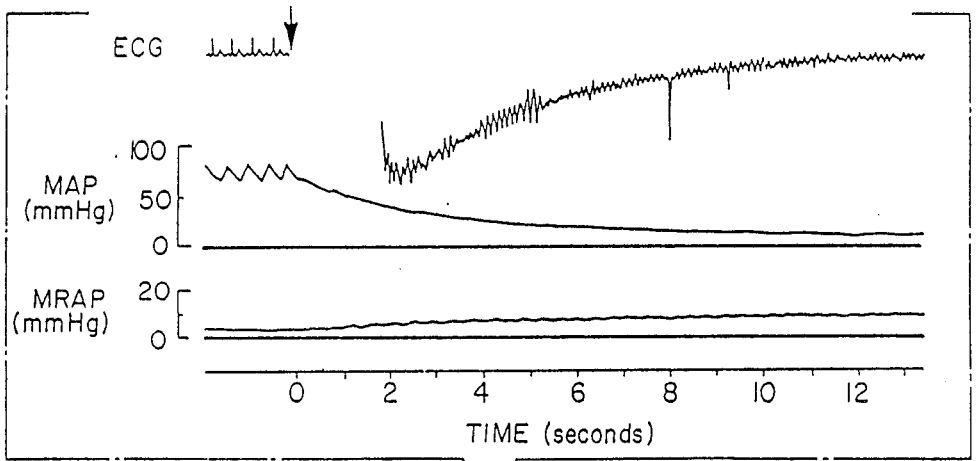
Figure 14:
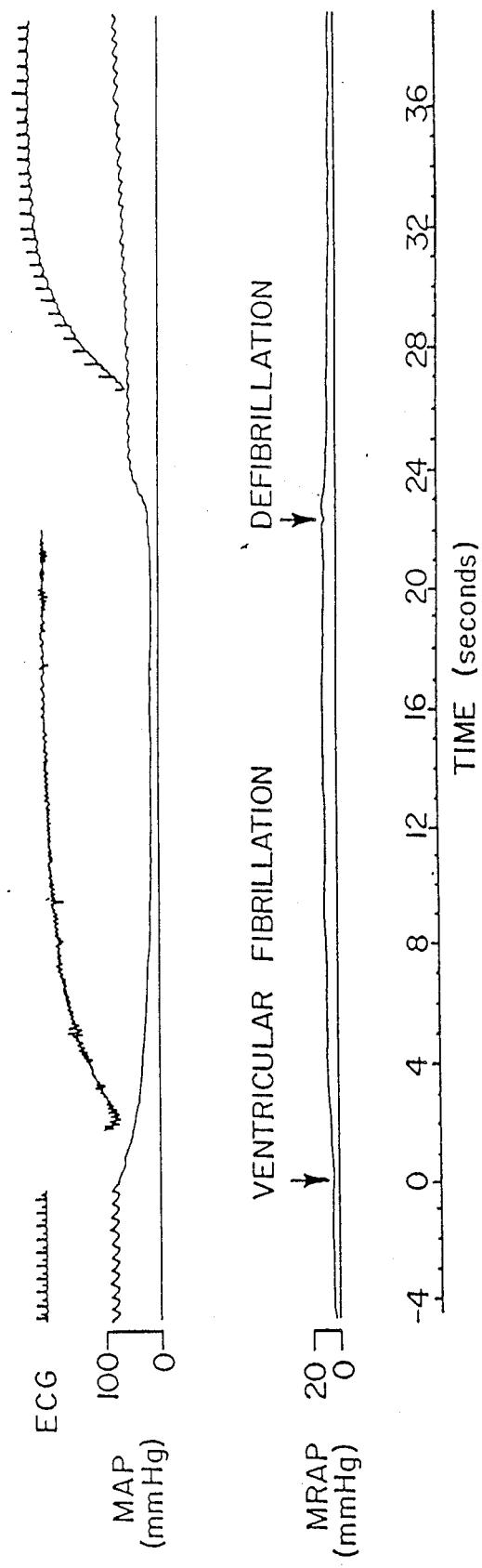
FIG. 14 is a graphical representation along a time axis similar to the graphical representation of FIG. 13, the time base having been expanded to show the affects on the R-wave, the MAP and MRAP which result from successful defibrillation.

An exemplary graphical representation of the ECG wave MAP and MRAP of one dog is illustrated in FIG. 11 along a time base of 15 seconds, the pacing rate in this case being 250 b.p.m. starting at time zero. The traces of MAP and MRAP indicate that the changes are slight; hemodynamic compromise is not indicated. As illustrated in FIG. 12, when the dog was subjected to a pacing rate of 280 b.p.m. starting at time zero, in this case as clearly shown by the traces, the MAP dropped markedly within two seconds and MRAP increased markedly within one second. Hemodynamic compromise prevailed. Thus, it is clear that the selected criteria can be sensed and properly form the basis of improved antitachycardia systems and methods. In FIG. 13, traces of MAP and MRAP of a dog whose heart has been placed in ventricular fibrillation at time zero clearly shows marked hemodynamic compromise, the traces of the MAP and MRAP indicating that MAP dropped and continued to drop to an extremely low level in about eight seconds, while the MRAP increased considerably within the same period. As sensing algorithms, a MRAP algorithm and a combined MRAP-rate algorithm were tested in this dog using a hand operated antitachycardia-defibrillator system. In FIG. 14, the ECG, MAP and MRAP traces of a dog whose heart was placed into ventricular fibrillation at time zero is shown for a time period of about 36 seconds, a defibrillating pulse having been applied after a time lapse of about 22 seconds. As shown in the MAP and MRAP traces of FIG. 14, considerable hemodynamics comprise appears from the onset of fibrillation and once the defibrillating pulse has been applied, is reversed. Moreover, normal beating rate was restored within about three seconds.

Rapid RVA pacing, simulating ventricular tachycardia, resulted in significant increases in MRAP ($5.5 \pm 0.5$ to $12.0 \pm 1.0$ mmHg., $p < 0.001$) and MRVP ($11.0 \pm 1.2$ to $16.0 \pm 0.9$ mmHg., $p < 0.02$) with marked hemodynamic compromise (MAP decreased from $85 \pm 6$ to $50 \pm 6$ mmHg., $p < 0.01$). These parameters remained stable during HRA pacing (simulating atrial tachycardia). The sensing algorithms successfully indicated those arrhythmias requiring termination, hemodynamically unstable ventricular tachycardia and fibrillation. Hemodynamically stable tachycardias were merely monitored, not manually terminated.

Thus, one can conclude that MRAP, MRVP and MAP, as well as other mean pressures, are useful in distinguishing hemodynamically significant tachycardias and could be used a sensed parameters in hemodynamically responsive antitachycardia systems.

The present invention provides significant advancements in the treatment of patients having malfunctioning hearts. The systems of the present invention operate automatically. The baseline pressure and permitted deviations therefrom are not based on an average of a large sampled population or standard; rather, these parameters are patient-specific.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. In a system for treating a malfunctioning heart of the type which includes storage means for storing electrical energy, electrode means for electrically coupling the storage means to the heart, pressure responsive sensing means for sensing pressure within at least one vessel between the heart and at least one lung, means for providing a first signal representative of baseline pressure, means responsive to output from the sensing means for developing a second signal representing mean current pressure over a period of given duration, and means responsive to output from the means for providing the first signal and output from the means for developing the second signal for charging and enabling discharge of the electrical energy stored by the storage means across the electrode means upon change in the mean current pressure of at least a predetermined amount from the representative baseline pressure.

2. The system according to claim 1, wherein the means providing a signal representative baseline pressure comprises means providing a signal representative of fixed baseline pressure.

3. The system according to claim 2, wherein said pressure responsive sensing means comprises sensing means for sensing pressure within a pulmonary artery.

4. The system according to claim 2, wherein said pressure responsive sensing means comprises sensing means for sensing pressure within a pulmonary vein.

5. The system according to claim 2, wherein said pressure responsive sensing means comprises means for sensing pulmonary capillary wedge pressure.

6. The system according to claim 1, wherein the means for providing a first signal representative of baseline pressure comprises means for developing a variable first signal representative of mean baseline pressure over a period of predetermined duration which is greater than the period of given duration.

7. The system according to claim 6, wherein said pressure sensing means comprises sensing means for sensing pressure within a pulmonary artery.

8. The system according to claim 6, wherein said pressure responsive sensing means comprises pressure within a pulmonary vein.

9. The system according to claim 6, wherein said pressure responsive sensing means comprises means for sensing pulmonary capillary wedge pressure.

10. The system according to claim 1, including means responsive to the first signal and to the second signal for providing a control signal indicative of the current mean pressure differing by at least a predetermined amount from the baseline pressure, and the means for charging and enabling discharge is responsive to the control signal.

11. The system according to claim 1, further comprising microprocessor for developing a control signal to control the means for charging and enabling discharge of the electrical energy stored by the storage means.

12. The system according to claim 1, including electrical means for sensing heart rate and producing a distinctive control signal upon the heart rate exceeding a predetermined rate, controllable antitachycardia pacemaking means for supplying pacing signals to the heart, controllable cardioverting/defibrillating means, including the storage means for storing electrical energy, control circuit means responsive to the distinctive control signal and to an output from the means for charging and enabling discharge to enable the antitachycardia pacemaking means in response to presence of the distinctive control signal and contemporaneous absence of the output and for enabling said cardioverting/defibrillating means in response to contemporaneous presence of both the distinctive control signal and the output.

13. The system according to claim 12, including means responsive to output from said electrical means for sensing heart rate for developing a discharge-synchronizing signal synchronized to an R-wave, and the means for discharging electrical energy across the electrode means and into the heart includes means for synchronizing the discharge with the discharge-synchronizing signal to effect cardioversion.

14. The system according to claim 13, wherein the means for discharging electrical energy across the electrode means and into the heart effects discharge on a nonsynchronized basis, in the absence of the synchronization signal, to effect defibrillation.

15. The system according to claim 1, including means for discharging electrical energy across said electrode means and into the heart effects discharge on a nonsynchronized basis to effect defibrillation.

16. A method of treating a malfunctioning heart comprising sensing pressure within a vessel between the heart and at least one lung, providing a representation of baseline pressure, determining mean current pressure from the sensed pressure at the site over a period of given duration, and delivering cardioverting/defibrillating electrical energy to the heart in response to change of at least a predetermined magnitude in the mean current pressure from the baseline pressure.

17. The method according to claim 16, wherein the step of providing a representation of baseline pressures comprises providing a fixed representation of baseline pressure.

18. The method according to claim 17, wherein the step of sensing pressure within a vessel comprises sensing pressure within a pulmonary artery.

19. The method according to claim 17, wherein the step of sensing pressure within a vessel comprises sensing pressure within a pulmonary vein.

20. The method according to claim 17, wherein the step of sensing pressure within a vessel comprises sensing pulmonary capillary wedge pressure.

21. The method according to claim 16, wherein the step of providing a representative of baseline pressure comprises providing a varying representation of baseline pressure over a period of predetermined duration which is greater than the period of given duration.

22. The method according to claim 21, wherein the step of sensing pressure within a vessel comprises sensing pressure within a pulmonary artery.

23. The method according to claim 21, wherein the step of sensing pressure within a vessel comprises sensing pressure within a pulmonary vein.

24. The method according to claim 21, wherein the step of sensing pressure within a vessel comprises sensing pulmonary capillary wedge pressure.

25. The method according to claim 16, wherein the step of delivering cardioverting/defibrillating electrical energy is taken upon mean current pressure differing from baseline pressure by at least the predetermined magnitude.

26. The method according to claim 16, including sensing heart rate, the step of delivering cardioverting/defibrillating electrical energy being taken upon the heart rate exceeding a given rate and the mean current pressure differing from baseline pressure by at least a predetermined magnitude.

27. In a system for treating a malfunctioning heart of the type which includes storage means for storing electrical energy, electrode means for electrically coupling the storage means to the heart, pressure responsive sensing means for sensing pressure within at least one vessel between the heart and at least one lung, means for providing a first signal representative of baseline pressure, means responsive to output from the sensing means for developing a second signal representing mean current pressure, and means responsive to output from the means for providing the first signal and output from the means for developing the second signal for charging and enabling discharge of the electrical energy stored by the storage means across the electrode means upon change in the mean current pressure of at least a predetermined amount from the representative baseline pressure.

28. A method of treating a malfunctioning heart comprising sensing pressure within a vessel between the heart and at least one lung, providing a representation of baseline pressure, determining means current pressure from the sensed pressure, and delivering cardioverting/defibrillating electrical energy to the heart in response to change of at least a predetermined magnitude in the mean current pressure from the baseline pressure.

29. A system for treating a malfunctioning heart comprising pressure responsive sensing means for sensing pressure within at least one vessel between the heart and at least one lung, means for providing a first signal representative of baseline pressure, means responsive to output from the sensing means for developing a second signal representing current pressure, and means responsive to output from the means for providing the first signal and output from the means for developing the second signal for enabling electrical means for correcting the malfunction upon change in the current pressure of at least a predetermined amount from the representative baseline pressure.

30. The system according to claim 29, wherein the means providing a signal representative baseline pressure comprises means providing a signal representative of fixed baseline pressure.

31. The system according to claim 30, wherein said pressure responsive sensing means comprises sensing means for sensing pressure within a pulmonary artery.

32. The system according to claim 30, wherein said pressure responsive sensing means comprises sensing means for sensing pressure within a pulmonary vein.

33. The system according to claim 30, wherein said pressure responsive sensing means comprises means for sensing pulmonary capillary wedge pressure.

34. The system according to claim 29, wherein the means for providing a first signal representative of baseline pressure comprises means for developing a variable first signal representative of mean baseline pressure over a period of predetermined duration which is greater than the period of given duration.

35. The system according to claim 34, wherein said pressure sensing means comprises means for sensing pressure within a pulmonary artery.

36. The system according to claim 34, wherein said pressure responsive sensing means comprises sensing means for sensing pressure within a pulmonary vein.

37. The system according to claim 34, wherein said pressure responsive sensing means comprises means for sensing pulmonary capillary wedge pressure.

* * * * *